(12) United States Patent
Kuczynski et al.

(10) Patent No.: US 10,794,822 B2
(45) Date of Patent: Oct. 6, 2020

(54) VERIFICATION OF THE QUALITY OF A LIQUID USING A QUALITY-SENSING BOTTLE CAP

(71) Applicant: International Business Machines Corporation, Armonk, NY (US)

(72) Inventors: Joseph Kuczynski, North Port, FL (US); Marvin M. Misgen, Rochester, MN (US); Debra Neuman-Horn, Rochester, MN (US); Joseph F. Prisco, Rochester, MN (US); Kevin J. Przybylski, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 405 days.

(21) Appl. No.: 15/815,793

(22) Filed: Nov. 17, 2017

(65) Prior Publication Data

US 2019/0154571 A1 May 23, 2019

(51) Int. Cl.
*G01N 21/3577* (2014.01)
*G01N 33/03* (2006.01)
(Continued)

(52) U.S. Cl.
CPC ....... *G01N 21/3577* (2013.01); *G01N 21/552* (2013.01); *G01N 21/85* (2013.01);
(Continued)

(58) Field of Classification Search
CPC .... G01N 33/03; G01N 33/0047; G01N 27/02; G01N 27/04; G01N 27/22; G01N 27/28; G01N 2030/884; G01N 2030/885
See application file for complete search history.

(56) References Cited

U.S. PATENT DOCUMENTS

| 5,089,139 A | 2/1992 | Asbeck |
| 8,679,559 B2 | 3/2014 | Bracco et al. |

(Continued)

FOREIGN PATENT DOCUMENTS

| WO | 2014181284 A1 | 11/2014 |
| WO | 2016141451 A1 | 9/2016 |

OTHER PUBLICATIONS

Guadarrama et al., "Array of sensors based on conducting polymers for the quality control of the aroma of the virgin olive oil," Sensors and Actuators B, vol. 69, 2000, pp. 276-282. (Year: 2000).*

(Continued)

*Primary Examiner* — Michael J Dalbo
(74) *Attorney, Agent, or Firm* — Matthew J. Bussan

(57) ABSTRACT

A quality-sensing bottle cap includes a sensor array having a plurality of conductive polymeric sensors. In some embodiments, each sensor is exposed within a mechanical chamber and is in electrical communication with an interrogation interface. The mechanical chamber is configured, in an inactive state, to be closed off from a headspace above a liquid contained in a bottle sealed with the quality-sensing bottle cap and configured, in an active state, to be open to the headspace. The sensor array may be tailored for a particular application, such as the detection of olive oil aroma. The sensor array may, for example, allow discrimination among olive oils of different qualities (e.g., extra virgin olive oil, lampante virgin olive oil, and refined olive oil), as well as discrimination among olive oils with negative attributes (e.g., olive oils with unpleasant aromatic notes, such as "fusty," "muddy sediment," "musty," and "rancid").

16 Claims, 12 Drawing Sheets

(51) Int. Cl.
| | |
|---|---|
| *G01N 21/85* | (2006.01) |
| *G01N 21/552* | (2014.01) |
| *G01N 21/35* | (2014.01) |
| *G01N 33/28* | (2006.01) |
| *G01N 21/53* | (2006.01) |

(52) U.S. Cl.
CPC ........... *G01N 33/03* (2013.01); *G01N 21/538* (2013.01); *G01N 33/2888* (2013.01); *G01N 2021/3595* (2013.01)

(56) References Cited

U.S. PATENT DOCUMENTS

| | | | |
|---|---|---|---|
| 2002/0141904 A1* | 10/2002 | Rosen | A61M 25/0612 422/550 |
| 2008/0199962 A1 | 8/2008 | Ippolito et al. | |
| 2009/0013769 A1 | 1/2009 | Larson et al. | |
| 2017/0184531 A1* | 6/2017 | Snelders | G01N 33/225 |
| 2018/0180554 A1* | 6/2018 | Huang | G01N 21/783 |

OTHER PUBLICATIONS

Michaelis, Kristen, "Your Extra-Virgin Olive Oil is Fake," www.foodrenegade.com, 4 pages, printed from <http://www.foodrenegade.com/your-extravirgin-olive-oil-fake/> on Jul. 31, 2017.

Stella et al., "Characterisation of olive oil by an electronic nose based on conducting polymer sensors," Sensors and Actuators B, vol. 63, 2000, pp. 1-9.

Chen et al., "A Polydiacetylenes-Based Sensor for Discriminating Oleic Acid from Stearic Acid and Elaidic Acid," Bull. Korean Chem. Soc., vol. 32, No. 10, 2011, pp. 3775-3778.

Guadarrama et al., "Array of sensors based on conducting polymers for the quality control of the aroma of the virgi olive oil," Sensors and Actuators B, vol. 69, 2000, pp. 276-282.

Unkown, "Chemical Characteristics," www.oliveoilsource.com, 9 pages, printed from <https://www.oliveoilsource.com/page/chemical-characteristics> on Aug. 3, 2017.

Wu et al., "3D-printed microelectronics for integrated circuitry and passive wireless sensors," Microsystems & Nanoengineering, vol. 1, Article No. 15013, 2015, 9 pages, downloaded from <http://www.nature.com/articles/micronano201513.pdf> on Jul. 31, 2017.

Unknown, "Interactive packaging," www.ifac.cnr.it, 2 pages, printed from <http://www.ifac.cnr.it/fosweb/index_file/Page718.htm> on Aug. 3, 2017.

Mignani et al., "A smart cap for olive oil rancidity detection using optochemical sensors," Proceedings of SPIE, vol. 6755, Article No. 67550V, 2007, 6 pages, downloaded from <http://proceedings.spiedigitallibrary.org/> on Aug. 22, 2016.

Unknown, "Sensory Analysis of Olive Oil: Method for the Organoleptic Assessment of Virgin Olive Oil," International Olive Council, COI/T.20/Doc. No. 15/Rev. 8, Nov. 2015, 20 pages.

Unknown, "Trade Standard Applying to Olive Oils and Olive Pomace Oils," International Olive Council, COI/T.15/NC No. 3/Rev. 11, Jul. 2016, 17 pages.

Hannon et al., "A Sensor Array for the Detection and Discrimination of Methane and Other Environmental Pollutant Gases," Sensors, vol. 16, Article No. 1163, 2016, 11 pages, downloaded from <http://www.mdpi.com/1424-8220/16/8/1163/pdf> on Nov. 6, 2017.

Hannon et al., "Supplementary Materials: A Sensor Array for the Detection and Discrimination of Methane and Other Environmental Pollutant Gases," Sensors, vol. 16, Article No. 1163, 2016, pp. S1-S4, downloaded from <http://www.mdpi.com/1424-8220/16/8/1163/s1> on Nov. 6, 2017.

* cited by examiner

VERIFICATION OF THE QUALITY OF A LIQUID USING A QUALITY-SENSING BOTTLE CAP

BACKGROUND

The present invention relates in general to materials verification. More particularly, the present invention relates to a quality-sensing bottle cap that includes a sensor array having a plurality of conductive polymeric sensors and to an electronic nose system that employs the quality-sensing bottle cap and an analytic unit. The present invention also relates to a method for analyzing a headspace above a liquid, such as extra virgin olive oil, contained in a bottle sealed with a quality-sensing bottle cap.

SUMMARY

In accordance with some embodiments of the present invention, a quality-sensing bottle cap includes a sensor array having a plurality of conductive polymeric sensors. Each sensor is exposed within a mechanical chamber and is in electrical communication with an interrogation interface. The mechanical chamber is configured, in an inactive state, to be closed off from a headspace above a liquid contained in a bottle sealed with the quality-sensing bottle cap and configured, in an active state, to be open to the headspace. The sensor array may be tailored for a particular application, such as the detection of olive oil aroma. The sensor array may, for example, allow discrimination among olive oils of different qualities (e.g., extra virgin olive oil, lampante virgin olive oil, and refined olive oil), as well as discrimination among olive oils with negative attributes (e.g., olive oils with unpleasant aromatic notes, such as "fusty," "muddy sediment," "musty," and "rancid").

BRIEF DESCRIPTION OF THE SEVERAL VIEWS OF THE DRAWINGS

Embodiments of the present invention will hereinafter be described in conjunction with the appended drawings, where like designations denote like elements.

DETAILED DESCRIPTION

Figure 1:
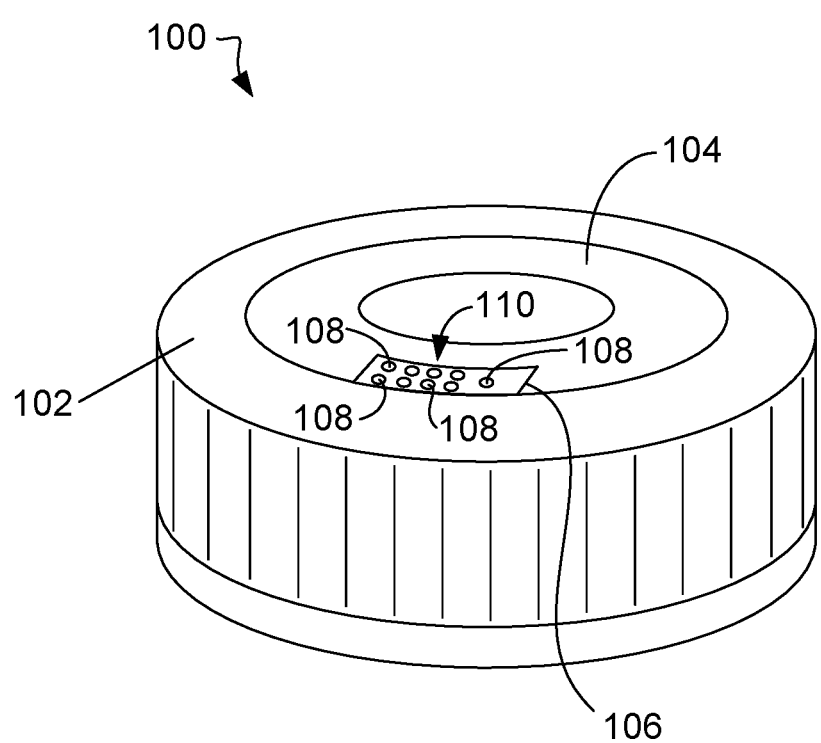
FIG. 1 is a perspective view of a quality-sensing bottle cap that includes a sensor array having a plurality of conductive polymeric sensors, in accordance with some embodiments of the present invention.

Verification of the quality of liquid food (e.g., olive oil, milk, and juice) sealed in a bottle is an area of intense interest. For example, a need exists for a consumer purchasing a bottle of extra virgin olive oil to be able to verify the quality of the product that he/she is purchasing and/or verify that the product is actually extra virgin olive oil. Such verification may, for example, be utilized to allay any concern that the consumer may have with respect to the product being adulterated or fake olive oil. Fraudsters have been known to add chlorophyll to sunflower and soybean oil and sell the resulting blended oil as extra virgin olive oil. Fraudsters have also been known to produce adulterated oil by blending extra virgin olive oil with at least one lower-grade oil. The lower-grade oil(s) may come in the form of lower-grade olive oil(s) (e.g., virgin olive oil, ordinary virgin olive oil, lampante virgin olive oil, and/or refined olive oil) and/or other type(s) of oil(s) (e.g., canola oil and/or colza oil). The adulterated oil may be chemically deodorized, colored, and/or flavored, and then may be sold by fraudsters as extra virgin olive oil.

The chemical composition of olive oil is different than that of other oils. For example, olive oil contains more oleic acid and less linoleic and linolenic acids than other vegetable oils. The relatively low linolenic acid level, for example, may be used as one factor in establishing authenticity of the olive oil. Other vegetable oils and seed oils such as canola oil have higher levels of linolenic acid. Likewise, the chemical composition of extra virgin olive oil is different than that of lower-grade olive oils. Free acidity, for example, may be used as one factor in establishing authenticity of extra virgin olive oil. Typically, laboratory testing has been required to discern whether a sample purported to be extra virgin olive oil is indeed authentic. Generally, one cannot depend on the human senses of taste and smell alone.

An electronic nose system utilizing a quality-sensing bottle cap and an analytic unit, in accordance with some embodiments of the present invention, can exploit such chemical composition differences to discern whether an olive oil is indeed genuine, or is fake or adulterated.

A quality-sensing bottle cap, in accordance with some embodiments of the present invention, includes a sensor array having a plurality of conductive polymeric sensors. Each sensor is exposed within a mechanical chamber and is in electrical communication with an interrogation interface. The mechanical chamber is configured, in an inactive state, to be closed off from a headspace above a liquid contained in a bottle sealed with the quality-sensing bottle cap and configured, in an active state, to be open to the headspace. The sensor array may be tailored for a particular application, such as the detection of olive oil aroma. The sensor array may, for example, allow discrimination among olive oils of different qualities (e.g., extra virgin olive oil, lampante virgin olive oil, and refined olive oil), as well as discrimination among olive oils with negative attributes (e.g., olive oils with unpleasant aromatic notes, such as "fusty," "muddy sediment," "musty," and "rancid").

The sensor array may include, for example, eight conductive polymeric sensors deposited electrochemically. Different electrodeposition conditions, different monomer, and/or different doping agents may be used to form respective ones of the conductive polymeric sensors. For example, in an embodiment, described below, of a sensor array tailored for the detection of olive oil aroma, eight conductive polymeric sensors based on three different polymeric base materials (i.e., poly-3-methylthiophene (P3MT), polypyrrole (PPy), and polyaniline (PANI)) are formed using three different monomers (i.e., 3-methylthiophene (3MTP), pyrrole, and aniline), three different electrochemical procedures (i.e., chronopotentiometry (CP), chronoamperometry (CA), and cyclic voltammetry (CV)), and six different electrolytes (i.e., lithium trifluoromethanesulfonate ($LiCF_3SO_3$), tetrabutylammonium tetrafluoroborate ($TBABF_4$), lithium perchlorate anhydrous ($LiClO_4$), tetrabutylammonium perchlorate (TBAP), hydrochloric acid (HCl), and tetrasulfonated nickel phthalocyanine (NiPcTs)). Each of the conductive polymeric sensors is deposited as a polymeric film (conductive polymer trace) grown directly onto a printed circuit board substrate between spaced-apart electrodes. The polymeric film grows first on the electrodes and then fills the gap between the electrodes.

The sensor array of the disclosed embodiment is "tailored" for detection of olive oil aroma through judicious selection of the eight conductive polymeric sensors. When exposed to the headspace of olive oil, each of the eight conductive polymeric sensors exhibits a measurable change in its conductivity (which may be measured as a change in electrical resistance or impedance) based on the presence of volatile organic components (VOCs) in the headspace. This change in conductivity, which shows good reproducibility and reversibility, allows discrimination among olive oils of different qualities (e.g., extra virgin olive oil, lampante virgin olive oil, and refined olive oil), as well as discrimination among olive oils with negative attributes (e.g., olive oils with unpleasant aromatic notes, such as "fusty," "muddy sediment," "musty," and "rancid").

In accordance with some embodiments of the invention, as the conductive polymer traces exhibit a change in electrical impedance based on the presence of volatile organic components in the headspace of an olive oil being verified, the output of each of the conductive polymer traces is routed through an interrogation interface (e.g., using conductive pads, inductive coupling, and/or wireless) to an analytic unit for conversion to digital data and analysis. The digital data may be analyzed, along with reference data associated with one or more olive oils each of known quality classification, using a multivariate statistical technique, such as principle component analysis (PCA), to determine a quality classification of the olive oil being verified.

Olive oil is composed mainly of triacylglycerols. Triacylglycerols, which are also referred to as triglycerides, are derived from the natural esterification of three fatty acid molecules and one glycerol molecule. Olive oil also contains small quantities of free fatty acid, glycerol, phosphatides, pigments, flavor compounds, sterols, and microscopic bits of olive. In fact, a typical olive oil contains more than 100 volatile organic components. These volatile organic components include, but are not limited to, acids, alcohols, esters, and carbonyls. Various aspects of production (e.g., olive soundness and health, olive freshness when pressed, oil freshness when bottled, and use of excessive heat) can impact the presence of these volatile organic components in olive oil.

Methods of analysis and standards for olive products are promulgated by the International Olive Council (IOC), which was formerly known as the International Olive Oil Council (IOOC). See, for example, "Trade Standard Applying to Olive Oils and Olive Pomace Oils," International Olive Council, COI/T.15/NC No 3/Rev. 11, July 2016.

Virgin olive oils are typically classified based on their organoleptic characteristics. Virgin olive oils of different qualities, listed from highest to lowest quality, include extra virgin olive oil, virgin olive oil, ordinary virgin olive oil, and lampante virgin olive oil.

The free acidity in olive oil is reflective of the formation of free fatty acids resulting from the breakdown of the triacylglycerols due to hydrolysis or lipolysis. Measurement of free fatty acidity (FFA) is conventionally done at a testing lab, with the results presented as grams of oleic acid per 100 grams olive oil.

"Extra virgin olive oil" has a free acidity, expressed as oleic acid, of not more than 0.8 g per 100 g, and the other characteristics of which correspond to those fixed for this category by the IOC standard.

"Virgin olive oil" has a free acidity, expressed as oleic acid, of not more than 2.0 g per 100 g, and the other characteristics of which correspond to those fixed for this category by the IOC standard.

"Ordinary virgin olive oil" has a free acidity of not more than 3.3 g per 100 g, and the other characteristics of which correspond to those fixed for this category by the IOC standard.

"Lampante virgin olive oil" has a free acidity, expressed as oleic acid, of more than 3.3 g per 100 g and/or the organoleptic characteristics and other characteristics of which correspond to those fixed for this category by the IOC standard. Lampante virgin olive oils possess negative (defective) attributes that make them unsuitable for human consumption.

Negative attributes of olive oil may be described using terms such as "fusty/muddy sediment," "musty-humid-earthy," "winey-vinegary," "acid-sour," "rancid," and "frostbitten olives (wet wood)" as defined by the IOC. See, for example, "Sensory Analysis of Olive Oil: Method for the Organoleptic Assessment of Virgin Olive Oil," International Olive Council, COI/T.20/Doc. No 15/Rev. 8, November 2015. The IOC provides the following definitions with respect to those terms:

Fusty/muddy sediment—"Characteristic flavour of oil obtained from olives piled or stored in such conditions as to have undergone an advanced stage of anaerobic fermentation, or of oil which has been left in contact with the sediment that settles in underground tanks and vats and which has undergone a process of anaerobic fermentation."

Musty-humid-earthy—"Characteristic moldy flavour of oils obtained from fruit in which large numbers of fungi and yeasts have developed as a result of its being stored in humid conditions for several days or of oil obtained from olives that have been collected with earth or mud on them and which have not been washed."

Winey-Vinegary—"Character flavour of certain oils reminiscent of wine or vinegar."

Acid-sour—"This flavour is mainly due to a process of aerobic fermentation in the olives or in olive paste left on pressing mats which have not been properly cleaned and leads to the formation of acetic acid, ethyl acetate and ethanol."

Rancid—"Flavour of oils which have undergone an intense process of oxidation."

Frostbitten olives (wet wood)—"Characteristic flavour of oils extracted from olives which have been injured by frost while on the tree."

"Refined olive oil" is olive oil obtained from virgin olive oils by refining methods which do not lead to alterations in the initial glyceridic structure. It has a free acidity, expressed as oleic acid, of not more than 0.3 g per 100 g and its other characteristics correspond to those fixed for this category by the IOC standard. Lampante virgin olive oils are often refined to produce refined olive oils.

"Olive oil composed of refined olive oil and virgin olive oils" is the oil consisting of a blend of refined olive oil and virgin olive oils fit for consumption as they are. It has a free acidity, expressed as oleic acid, of not more than 1 g per 100 g and its other characteristics correspond to those fixed for this category by the IOC standard An electronic nose system utilizing a quality-sensing bottle cap and an analytic unit, in accordance with some embodiments of the present invention, can exploit chemical composition differences to discriminate among olive oils of different qualities (e.g., extra virgin olive oil, lampante virgin olive oil, and refined olive oil), as well as discriminate among olive oils with different negative attributes (e.g., olive oils with unpleasant aromatic notes, such as "fusty," "muddy sediment," "musty," and "rancid").

Conductive polymeric sensors may be selected for inclusion in the sensor array based on a number of criteria. Those criteria include, but are not limited to, suitable levels of selectivity toward one or more of the volatile components (VOCs) that may be present in the headspace of olive oil (including olive oils of different quality classifications, as well as olive oils with different negative attributes), stability, reproducibility, and reversibility.

With regard to selectivity, the electrical impedance of different ones of the conductive polymeric sensors will preferably change upon exposure to the various VOCs that are typically present in the headspace of olive oil with different quality classifications, as well as olive oil with different negative attributes. For example, a first set of one or more of the conductive polymeric sensors included in the sensor array may exhibit a decrease in electrical impedance upon exposure to one or more of the various VOCs that may be present in the headspace of olive oils, while a second set (different than the first set) of one or more of the conductive polymeric sensors included in the sensor array may exhibit an increase in electrical impedance upon exposure to the same one or more VOCs.

With regard to stability, the electrical impedance of each conductive polymeric sensor included in the sensor array is preferably stable over a suitable amount of time (e.g., the typical shelf life of a bottle of olive oil). Also, the electrical impedance of each conductive polymeric sensor included in the sensor array is preferably stable over a suitable range of temperatures (e.g., from 20° C. to 30° C.).

With regard to reproducibility, the electrical impedance of each conductive polymeric sensor included in the sensor array when exposed to the VOCs present in the headspace of olive oil preferably will not vary substantially from measurement to measurement for the same olive oil.

With regard to reversibility, the electrical impedance of each conductive polymeric sensor included in the sensor array preferably returns substantially to its original pre-exposure electrical impedance when no longer exposed to the VOCs present in the headspace of olive oil.

Figure 2:
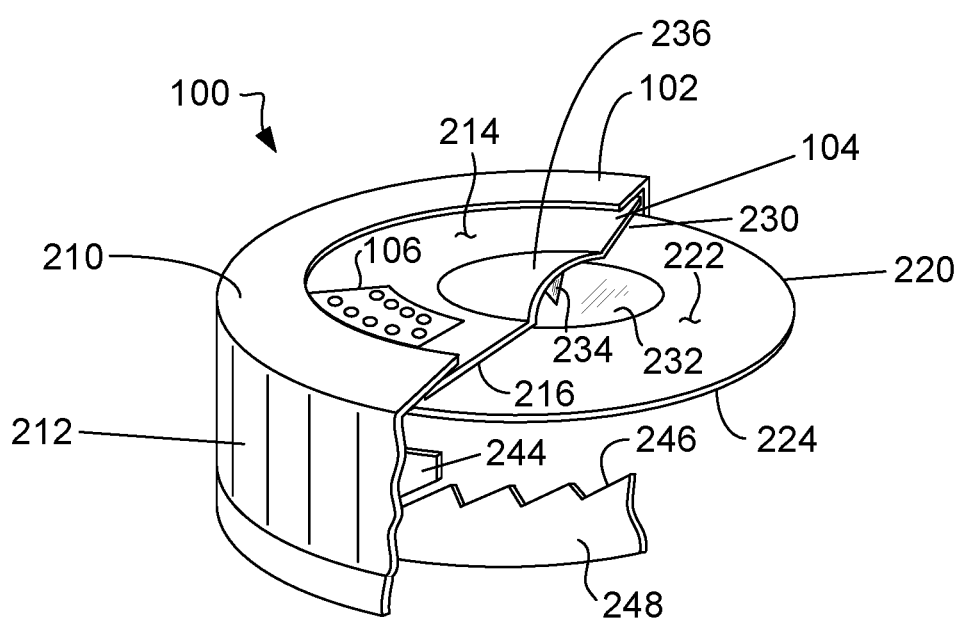
FIG. 2 is a partial cut-away perspective view of the quality-sensing bottle cap of FIG. 1.
Figure 3:
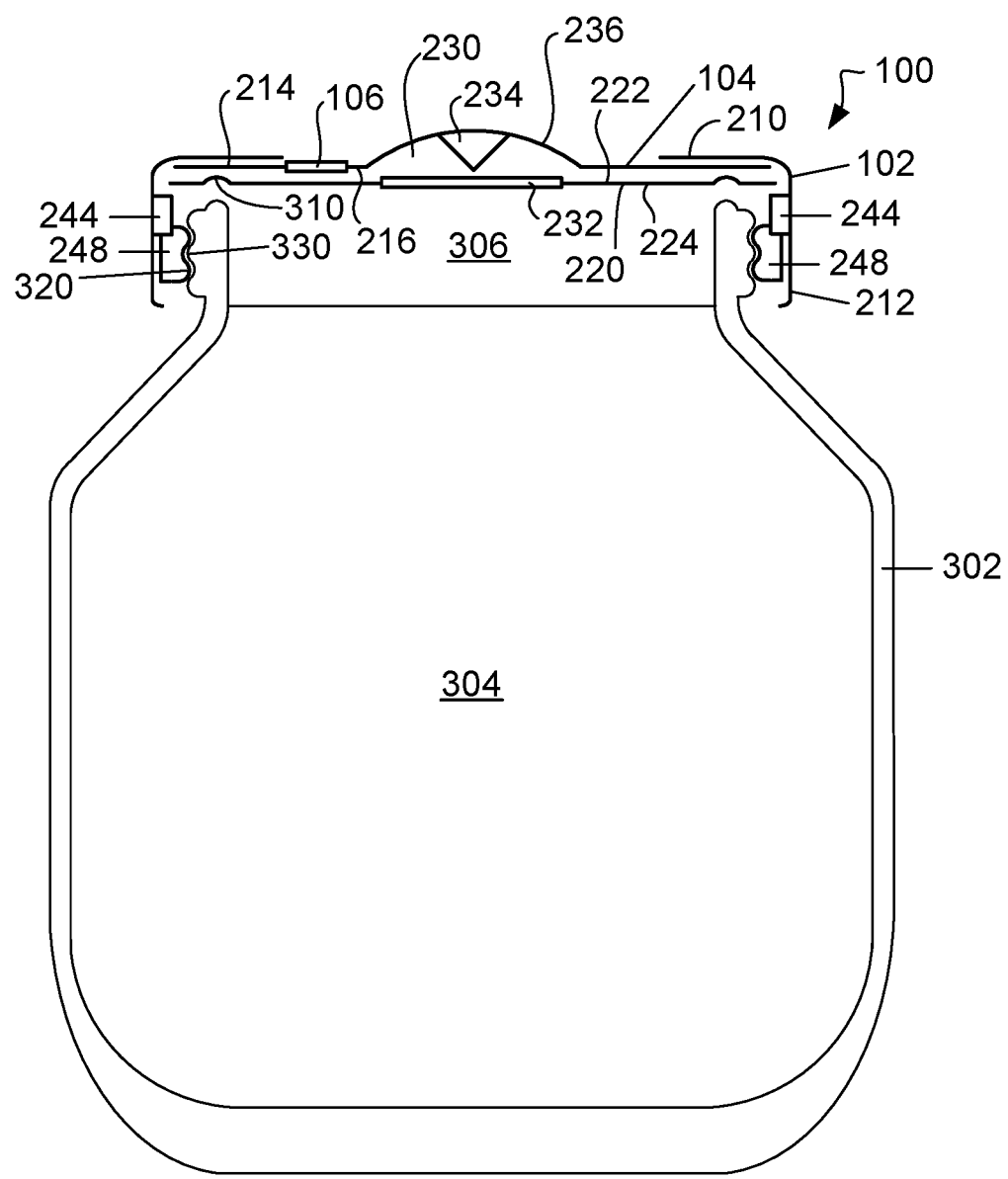
FIG. 3 is a cross-sectional elevational view of the quality-sensing bottle cap of FIG. 1 threaded atop a bottle containing a liquid, in accordance with some embodiments of the present invention.

FIG. 1 is a perspective view of a quality-sensing bottle cap 100 that includes a sensor array having a plurality of conductive polymeric sensors, in accordance with some embodiments of the present invention. FIG. 2 is a partial cut-away perspective view of the quality-sensing bottle cap 100 of FIG. 1. FIG. 3 is a cross-sectional elevational view of the quality-sensing bottle cap 100 of FIG. 1 threaded atop a bottle 302 containing a liquid 304, such as extra virgin olive oil, in accordance with some embodiments of the present invention.

As illustrated in FIG. 1, an overcap ring 102 and a top seal lid 104 are visible on the exterior of the quality-sensing bottle cap 100. The overcap ring 102 may be made of metal, plastic, or combinations thereof. Likewise, the top seal lid 104 may be made of metal, plastic, or combinations thereof. A printed circuit board substrate 106, the top surface of which is also visible on the exterior of the quality-sensing bottle cap 100, is integrated into the top seal lid 104. For example, in an embodiment where the top seal lid 104 is plastic, the printed circuit board substrate 106 may be insert molded into the top seal lid 104. In an embodiment where the top seal lid 104 is metal, the printed circuit board may be potted (e.g., using a thermosetting plastic or a silicone rubber gel) into a hole that extends through the top seal lid 104.

The top surface of the printed circuit board substrate 106 includes a plurality of conductive pads 108 that together define an interrogation interface 110. The interrogation interface 110 may include, for example, a power-in contact and a plurality of sensor-out contacts. The conductive pads 108 are in electrical communication (e.g., using plated through hole vias and conductive metal traces) with a plurality of conductive polymeric sensors (e.g., S1-S8 in FIG. 4) that together define a sensor array (e.g., 400 in FIG. 4) disposed on the bottom surface of the printed circuit board substrate 106. The printed circuit board substrate 106 may, for example, correspond to the printed circuit board substrate 405 of FIGS. 4 and 5, described below.

In the embodiment illustrated in FIG. 1, the interrogation interface 110 takes the form of a plurality of conductive pads 108. One skilled in the art will appreciate, however, that the interrogation interface may take other forms. For example, inductive coupling and/or wireless may be utilized to provide the interrogation interface in lieu of, or in addition to, one or more conductive pads.

Now referring to FIGS. 2 and 3, the overcap ring 102 ring includes a horizontal portion 210 and a vertical portion 212. The top seal lid 104 is circular and includes an upper surface 214 and a lower surface 216. The top seal lid 104 is configured to be received in the overcap ring 102 such that a peripheral portion of the upper surface 214 of the top seal lid 104 engages the horizontal portion 210 of the overcap ring 102.

In addition to the overcap ring 102 and the top seal lid 104, the quality-sensing bottle cap 100 also includes a main bottle seal lid 220. The main bottle seal lid 220 may be made of metal, plastic, or combinations thereof. The main bottle seal lid 220 is circular and includes a top side 222 and an underside 224. The main bottle seal lid 220 is configured to be received in the overcap ring 102 between the top seal lid 104 and the upper portion of the bottle 302 (shown in FIG. 3). The underside 224 of the main bottle seal lid 220 includes a sealing ring 310 (shown in FIG. 3) configured to engage the upper portion of the bottle 302 to seal the bottle 302. The sealing ring 310 may, for example, include a coating of elastomeric sealing material.

A mechanical chamber 230 is defined between the lower surface 216 of the top seal lid 104 and the top side 222 of the main bottle seal lid 220. Each of a plurality of conductive polymeric sensors (e.g., S1-S8 in FIG. 4) is exposed within the mechanical chamber 230. The conductive polymeric sensors may be deposited on the bottom surface of the printed circuit board substrate 106 in the form of conductive polymer traces.

The mechanical chamber 230 is configured, in an inactive state, to be closed off from a headspace 306 (shown in FIG. 3) above the liquid 304 (shown in FIG. 3) contained in the bottle 302 and configured, in an active state, to be open to the headspace 306. In the embodiment illustrated in FIGS. 2 and 3, the main bottle seal lid 220 includes a septum 232 that separates the mechanical chamber 230 from the headspace 306 in the inactive state, and the top seal lid 104 includes a protruding element 234 configured to be capable of piercing the septum 232 to drive the mechanical chamber 230 from the inactive state to the active state. The protruding element 234 may pierce the septum 232, for example, when a bump-out area 236 of the top seal lid 104 is pressed down or when the overcap ring 102 is pressed down toward the bottle 302 (e.g., prior to twisting off the quality-sensing bottle cap 100 using a "press down and twist" safety cap mechanism, described below). The septum 232 may be any suitable material. For example, the septum 232 may be a metal foil (i.e., single-use). More preferably, however, the septum 232 is an elastomeric self-sealing septum (i.e., multiple-use) that permits the mechanical chamber 230 to return to the inactive state after being driven to the active state. The protruding element 234 may be a knife edge as illustrated in FIGS. 2 and 3, or may be a solid or perforated hollow needle.

The septum 232 may be adhered to or integrated into the main bottle seal lid 220. For example, the septum 232 may be adhered (e.g., using a pressure sensitive adhesive) over a hole that extends through the main bottle seal lid 220. Alternatively, in an embodiment where the main bottle seal lid 220 is plastic, the septum 232 may be insert molded into the main bottle seal lid 220.

The protruding element 234 may be adhered to or integrated into the top seal lid 104. For example, the protruding element 232 may be adhered (e.g., using an epoxy adhesive) to the lower surface 216 of the top seal lid 104. Alternatively, in an embodiment where the top seal lid 104 is plastic, the protruding element 234 may be insert molded into the top seal lid 104. The top seal lid 104 may be configured to accommodate the protruding element 234. For example, in the embodiment illustrated in FIGS. 2 and 3, the top seal lid 104 includes a bump-out area 236 in which the protruding element 234 resides.

The vertical portion 212 of the overcap ring 102 includes a plurality of projections 244 configured to selectively engage a sawtooth engagement surface 246 formed on a threaded ring 248. The threaded ring 248 may be made of metal, plastic, or combinations thereof. The threaded ring 248 includes screw-on threads 320 (shown in FIG. 3) configured to mate with screw-on threads 330 (shown in FIG. 3) formed on an upper surface of the bottle 302. The projections 244 of the overcap ring 102 and the sawtooth engagement surface 246 of the threaded ring 248 together provide a "press down and twist" safety cap mechanism. The projections 244 of the overcap ring 102 effectively engage the sawtooth engagement surface 246 of the threaded ring 248 for rotation only when the overcap ring 102 is pressed down toward the bottle 302. Twisting of the overcap ring 102 (without pressing down) will not rotate the threaded ring 248.

Figure 4:
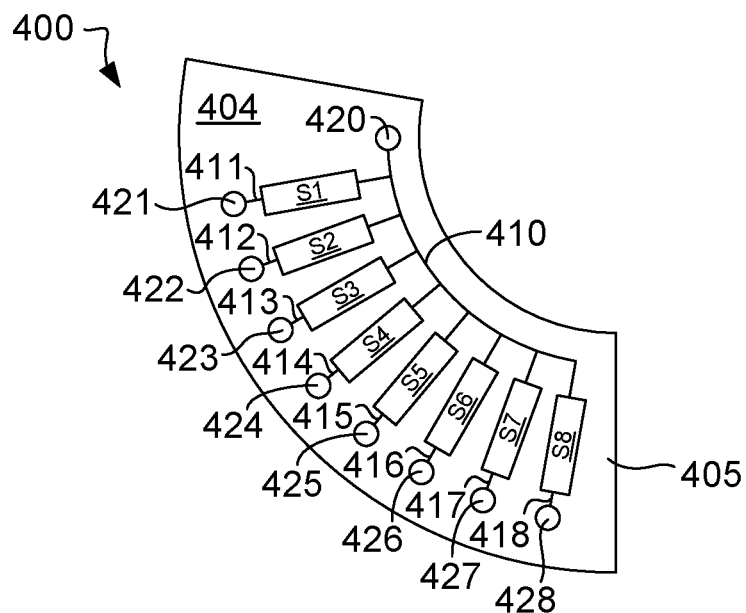
FIG. 4 is a top view of a sensor array having a plurality of conductive polymeric sensors in the form of conductive polymer traces deposited on the bottom surface of the printed circuit board substrate, in accordance with some embodiments of the present invention.

FIG. 4 is a top view of a sensor array 400 having eight conductive polymeric sensors S1-S8 in the form of eight conductive polymer traces deposited on the bottom surface 404 of a printed circuit board substrate 405, in accordance with some embodiments of the present invention. Each of the eight conductive polymer traces is electrochemically deposited, as described in detail below, between two space-apart conductive metal traces. For example, the conductive polymeric sensor S1 is produced by electrochemically depositing (via electropolymerization) a conductive polymer trace between the conductive metal traces 410 and 411. Similarly, the conductive polymeric sensors S2-S8 are respectively produced by electrochemically depositing a conductive polymer trace between the conductive metal traces 410 and 412, 410 and 413, 410 and 414, 410 and 415, 410 and 416, 410 and 417, and 410 and 418. Plated through hole vias 420-428 respectively connect the conductive metal traces 410-418 to conductive pads (P and C1-C8 in FIG. 5) deposited on the top surface (504 in FIG. 5) of the printed circuit board substrate 405.

Figure 5:
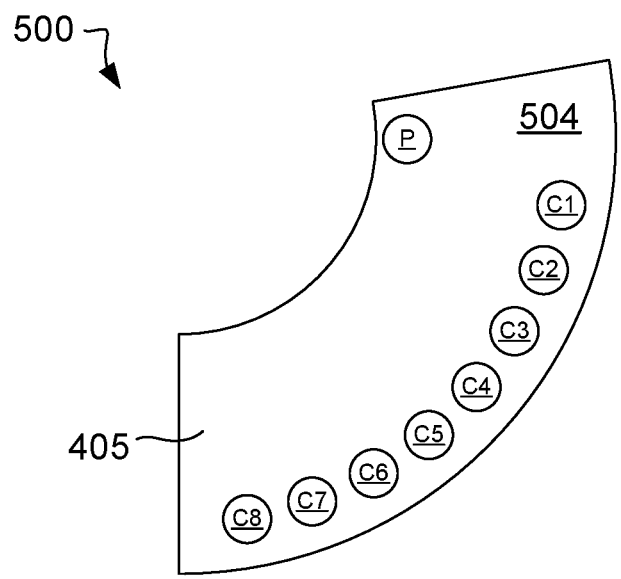
FIG. 5 is a top view of an interrogation interface having a power-in contact and a plurality of sensor-out contacts in the form of conductive pads deposited on the top surface of the printed circuit board substrate of FIG. 4, in accordance with some embodiments of the present invention.

FIG. 5 is a top view of an interrogation interface 500 having a power-in contact P and a plurality of sensor-out contacts C1-C8 in the form of conductive pads deposited on the top surface 504 of the printed circuit board substrate 405 of FIG. 4, in accordance with some embodiments of the present invention. The power-in contact P is in electrical communication (e.g., by the plated through hole via 420 and the conductive meal trace 410 of FIG. 4) with a first side of all of the conductive polymeric sensors (S1-S8 of FIG. 4). Each of the sensor-out contacts C1-C8 is in electrical communication (e.g., by the plated through hole vias 421-428 and the conductive metal traces 411-418 of FIG. 4) with a second side of a respective one of the conductive polymeric sensors (S1-S8 of FIG. 4).

The eight conductive polymeric sensors selected for inclusion in the exemplary sensor array illustrated in FIG. 4 are based on modified versions of the polymeric sensors disclosed in Guadarrama et al., "Array of sensors based on conducting polymers for the quality control of the aroma of the virgin olive oil," Sensors and Actuators B, Vol. 69, 2000, pp. 276-282, which is hereby incorporated herein by reference in its entirety. One skilled in the art will appreciate, however, that other conductive polymeric sensors may be selected in lieu of, or in addition to, those selected for inclusion in the exemplary sensor array illustrated in FIG. 4. One skilled in the art will also appreciate that other sensor array configurations may be employed in lieu of that used in the exemplary sensor array illustrated in FIG. 4. For example, any number of conductive polymeric sensors may be used in lieu of eight.

The conductive polymeric sensors included in the exemplary sensor array illustrated in FIG. 4 may be synthesized using the processes disclosed in the Guadarrama et al. article, supra, for preparation of its polymeric sensors. One skilled in the art will appreciate, however, that the conductive polymeric sensors may be synthesized by other processes or obtained commercially. For example, processes for preparation of chemically (C) and electrochemically (EC) produced sensors in an array of conducting polymer sensors are disclosed in Stella et al., "Characterisation of olive oil by an electronic nose based on conducting polymer sensors," Sensors and Actuators B, Vol. 63, 2000, pp. 1-9, which is hereby incorporated herein by reference in its entirety. A prophetic synthetic procedure for producing each of the respective conductive polymeric sensors included in the exemplary sensor array illustrated in FIG. 4 is set forth below.

The prophetic synthetic procedure utilizes electropolymerization to grow polymeric films, one for each of the respective conductive polymeric sensors included in the exemplary sensor array illustrated in FIG. 4. Electrochemical measurements are performed during the electropolymerization and at other times during the prophetic synthetic procedure. The electropolymerization and the electrochemical measurements may be performed in a conventional three electrode cell, such as the Princeton Applied Research/EG&G Model 263 Potentiostat/Galvanostat. The three electrode cell includes a working electrode, a reference electrode, and a counter electrode. Electropolymerization takes place when two electrodes (e.g., conductive metal traces 410, 411 in FIG. 4) separated from each other by a suitable gap (also referred to herein as "electrode spacing") are short-circuited to act as a single working electrode. The substrate is masked to confine the deposition to a sensing area and placed in the conventional three electrode cell together with an Ag/AgCl reference electrode (when an aqueous media is used) or an $Ag/AgNO_3$ reference electrode (when a non-aqueous media is used), as well as a counter electrode. The counter electrode may be, for example, a large surface area platinum gauze, which may be flamed prior to use. During the prophetic synthetic procedure, the various potentials (e.g., $E_f$) are measured relative to the corresponding reference electrode.

During electropolymerization, the polymeric films may be grown at a constant temperature, typically 25° C. The constant temperature may be maintained, for example, using an electrochemical cell having a thermostatic jacket and a temperature controlled liquid system. The electrolytic solutions utilized in the prophetic synthetic procedure may be deoxygenated prior to use by bubbling nitrogen gas through the solutions for 10 min.

Sensor One (S1)
Polymer: poly-3-methylthiophene (P3MT)
Electrochemical procedure: chronopotentiometry (CP)
Monomer: 3-methylthiophene (3MTP)
Electrolyte: lithium trifluoromethanesulfonate ($LiCF_3SO_3$)

Sensor S1 may be obtained from an electrolytic solution of 3-methylthiophene (3MTP) 0.1 mol/L in acetonitrile, using lithium trifluoromethanesulfonate ($LiCF_3SO_3$) 0.1 mol/L as an electrolyte. The triflate anion ($CF_3SO_3^-$) serves as a doping anion in sensor S1. The $P3MT/LiCF_3SO_3$ film of sensor S1 may be grown (i.e., deposited onto a substrate between two separated electrodes) via a chronopotentiometry (CP) operation, followed by a conditioning operation. The chronopotentiometry operation may be performed at a constant current (i) of −0.6 mA for 60 s. This produces a stable oxidized blue film. The subsequent conditioning operation may be performed to obtain the $P3MT/LiCF_3SO_3$ film of sensor S1 in a reduced state by biasing the film to a potential ($E_f$) of −0.5 V for 60 s.

The $P3MT/LiCF_3SO_3$ film of sensor S1 may be grown electrochemically (via chronopotentiometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The $P3MT/LiCF_3SO_3$ film of sensor S1 may be, for example, grown via chronopotentiometry on the substrate 405 illustrated in FIG. 4 having conductive metal traces 410, 411 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 411 and then fills the gap between the conductive metal traces 410, 411. Once the $P3MT/LiCF_3SO_3$ film of sensor S1 has been deposited, the substrate may be removed from the solution, and then washed with acetonitrile.

A masking material may be used to confine the deposition of the $P3MT/LiCF_3SO_3$ film of sensor S1 to a sensing area on the substrate designated for sensor S1. For example, a glass membrane (or other masking material) with a central opening that defines the sensing area may be provided on the substrate during the deposition of the $P3MT/LiCF_3SO_3$ film of sensor S1, and then removed. Prior to depositing the $P3MT/LiCF_3SO_3$ film of sensor S1, the substrate may be cleaned with acetone, and rinsed with distilled water.

Optionally, prior to depositing the $P3MT/LiCF_3SO_3$ film of sensor S1, the sensing area may be treated with hexamethyldisilazane (HMDS) or other suitable coupling agent to improve the adhesion of the $P3MT/LiCF_3SO_3$ film of sensor S1 to the substrate.

Sensor Two (S2)
Polymer: poly-3-methylthiophene (P3MT)
Electrochemical procedure: chronopotentiometry (CP)
Monomer: 3-methylthiophene (3MTP)
Electrolyte: tetrabutylammonium tetrafluoroborate (TBABF$_4$)

Sensor S2 may be obtained from an electrolytic solution of 3-methylthiophene (3MTP) 0.1 mol/L in acetonitrile, using tetrabutylammonium tetrafluoroborate (TBABF$_4$) 0.1 mol/L as an electrolyte. The tetrafluoroborate anion (BF$_4^-$) serves as a doping anion in sensor S2. The P3MT/TBABF$_4$ film of sensor S2 may be grown (i.e., deposited onto a substrate between two separated electrodes) via a chronopotentiometry (CP) operation, followed by a conditioning operation. The chronopotentiometry operation may be performed at a constant current (i) of −0.6 mA for 60 s. This produces a stable oxidized blue film. The subsequent conditioning operation may be performed to obtain the P3MT/TBABF$_4$ film of sensor S2 in a reduced state by biasing the film to a potential (E$_f$) of −0.5 V for 60 s.

The P3MT/TBABF$_4$ film of sensor S2 may be grown electrochemically (via chronopotentiometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The P3MT/TBABF$_4$ film of sensor S2 may be, for example, deposited on the substrate 405 illustrated in FIG. 4 having conductive metal traces 410, 412 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 412 and then fills the gap between the conductive metal traces 410, 412. Once the P3MT/TBABF$_4$ film of sensor S2 has been deposited, the substrate may be removed from the solution, and then washed with acetonitrile.

A masking material may be used to confine the deposition of the P3MT/TBABF$_4$ film of sensor S2 to a sensing area on the substrate designated for sensor S2. For example, a glass membrane (or other masking material) with a central opening that defines the sensing area may be provided on the substrate during the deposition of the P3MT/TBABF$_4$ film of sensor S2, and then removed. Prior to depositing the P3MT/TBABF$_4$ film of sensor S2, the substrate may be cleaned with acetone, and rinsed with distilled water.

Optionally, prior to depositing the P3MT/TBABF$_4$ film of sensor S2, the sensing area may be treated with hexamethyldisilazane (HMDS) or other suitable coupling agent to improve the adhesion of the P3MT/TBABF$_4$ film of sensor S2 to the substrate.

Sensor Three (S3)
Polymer: poly-3-methylthiophene (P3MT)
Electrochemical procedure: chronopotentiometry (CP)
Monomer: 3-methylthiophene (3MTP)
Electrolyte: lithium perchlorate anhydrous (LiClO$_4$)

Sensor S3 may be obtained from an electrolytic solution of 3-methylthiophene (3MTP) 0.1 mol/L in acetonitrile, using lithium perchlorate anhydrous (LiClO$_4$) 0.1 mol/L as an electrolyte. The perchlorate anion (ClO$_4^-$) serves as a doping anion in sensor S3. The P3MT/LiClO$_4$ film of sensor S3 may be grown (i.e., deposited onto a substrate between two separated electrodes) via a chronopotentiometry (CP) operation, followed by a conditioning operation. The chronopotentiometry operation may be performed at a constant current (i) of −0.6 mA for 60 s. This produces a stable oxidized blue film. The subsequent conditioning operation may be performed to obtain the P3MT/LiClO$_4$ film of sensor S3 in a reduced state by biasing the film to a potential (E$_f$) of −0.5 V for 60 s.

The P3MT/LiClO$_4$ film of sensor S3 may be grown electrochemically (via chronopotentiometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The P3MT/LiClO$_4$ film of sensor S3 may be, for example, deposited on the substrate 405 illustrated in FIG. 4 having conductive metal traces 410, 413 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 413 and then fills the gap between the conductive metal traces 410, 413. Once the P3MT/LiClO$_4$ film of sensor S3 has been deposited, the substrate may be removed from the solution, and then washed with acetonitrile.

A masking material may be used to confine the deposition of the P3MT/LiClO$_4$ film of sensor S3 to a sensing area on the substrate designated for sensor S3. For example, a glass membrane (or other masking material) with a central opening that defines the sensing area may be provided on the substrate during the deposition of the P3MT/LiClO$_4$ film of sensor S3, and then removed. Prior to depositing the P3MT/LiClO$_4$ film of sensor S3, the substrate may be cleaned with acetone, and rinsed with distilled water.

Optionally, prior to depositing the P3MT/LiClO$_4$ film of sensor S3, the sensing area may be treated with hexamethyldisilazane (HMDS) or other suitable coupling agent to improve the adhesion of the P3MT/LiClO$_4$ film of sensor S3 to the substrate.

Sensor Four (S4)
Polymer: poly-3-methylthiophene (P3MT)
Electrochemical procedure: chronopotentiometry (CP)
Monomer: 3-methylthiophene (3MTP)
Electrolyte: tetrabutylammonium perchlorate (TBAP)

Sensor S4 may be obtained from an electrolytic solution of 3-methylthiophene (3MTP) 0.1 mol/L in acetonitrile, using tetrabutylammonium perchlorate TBAClO$_4$ [also referred to as "TBAP"] 0.1 mol/L as an electrolyte. The perchlorate anion (ClO$_4^-$) serves as a doping anion in sensor S4. The P3MT/TBAClO$_4$ film of sensor S4 may be grown (i.e., deposited onto a substrate between two separated electrodes) via a chronopotentiometry (CP) operation, followed by a conditioning operation. The chronopotentiometry operation may be performed at a constant current (i) of −0.6 mA for 60 s. This produces a stable oxidized blue film. The subsequent conditioning operation may be performed to obtain the P3MT/TBAClO$_4$ film of sensor S4 in a reduced state by biasing the film to a potential (E$_f$) of −0.5 V for 60 s.

The P3MT/TBAClO$_4$ film of sensor S4 may be grown electrochemically (via chronopotentiometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The P3MT/TBAClO$_4$ film of sensor S4 may be, for example, deposited on the substrate 405 illustrated in FIG. 4 having conductive metal traces 410, 414 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 414 and then fills the gap between the conductive metal traces 410, 414. Once the P3MT/TBAClO$_4$ film of sensor S4 has been deposited, the substrate may be removed from the solution, and then washed with acetonitrile.

A masking material may be used to confine the deposition of the P3MT/TBAClO$_4$ film of sensor S4 to a sensing area on the substrate designated for sensor S4. For example, a glass membrane (or other masking material) with a central opening that defines the sensing area may be provided on the substrate during the deposition of the P3MT/TBAClO$_4$ film of sensor S4, and then removed. Prior to depositing the P3MT/TBAClO$_4$ film of sensor S4, the substrate may be cleaned with acetone, and rinsed with distilled water.

Optionally, prior to depositing the P3MT/TBAClO$_4$ film of sensor S4, the sensing area may be treated with hexamethyldisilazane (HMDS) or other suitable coupling agent to improve the adhesion of the P3MT/TBAClO$_4$ film of sensor S4 to the substrate.

Sensor Five (S5)
Polymer: polyaniline (PANI)
Electrochemical procedure: chronoamperometry (CA)
Monomer: analine
Electrolyte: hydrochloric acid (HCl).

Sensor S5 may be obtained from an electrolytic solution of aniline 1.0 mol/L and HCl 2.0 mol/L in deionized water. The chlorine anion (Cl$^-$) serves as a doping anion in sensor S5. The PANI/HCl film of sensor S5 may be grown (i.e., deposited onto a substrate between two separated electrodes) via a chronoamperometry (CA) operation, followed by a conditioning operation. The chronoamperometry operation may be performed at a constant potential ($E_{pol}$) of 0.9 V for 120 s. The subsequent conditioning operation may be performed to obtain the PANI/HCl film of sensor S5 by biasing the film to a potential ($E_f$) of 0.9 V for 60 s.

The PANI/HCl film of sensor S5 may be grown electrochemically (via chronoamperometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The PANI/HCl film of sensor S5 may be, for example, deposited on the substrate 405 illustrated in FIG. 4 having conductive metal traces 410, 415 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 415 and then fills the gap between the conductive metal traces 410, 415. Once the PANI/HCl film of sensor S5 has been deposited, the substrate may be removed from the solution, and then washed with acetonitrile.

A masking material may be used to confine the deposition of the PANI/HCl film of sensor S5 to a sensing area on the substrate designated for sensor S5. For example, a glass membrane (or other masking material) with a central opening that defines the sensing area may be provided on the substrate during the deposition of the PANI/HCl film of sensor S5, and then removed. Prior to depositing the PANI/HCl film of sensor S5, the substrate may be cleaned with acetone, and rinsed with distilled water.

Optionally, prior to depositing the PANI/HCl film of sensor S5, the sensing area may be treated with hexamethyldisilazane (HMDS) or other suitable coupling agent to improve the adhesion of the PANI/HCl film of sensor S5 to the substrate.

Sensor Six (S6)
Polymer: polypyrrole (PPy)
Electrochemical procedure: chronoamperometry (CA)
Monomer: pyrrole
Electrolyte: tetrasulfonated nickel phthalocyanine (NiPcTs)

Sensor S6 may be obtained from an electrolytic solution of pyrrole 0.1 mol/L and nickel(II) phthalocyanine-tetrasulfonic acid tetrasodium salt (NiPcTs) 0.01 mol/L in deionized water. Anions of nickel phthalocyanine tetrasulfonic acid, such as the tetra-anion [NiPc]$^{4-}$, serve as doping anions in sensor S6. The PPy/NiPcTs film of sensor S6 may be grown (i.e., deposited onto a substrate between two separated electrodes) via a chronoamperometry (CA) operation, followed by a conditioning operation. The chronoamperometry operation may be performed at a constant potential ($E_{pol}$) of 0.9 V for 120 s. The subsequent conditioning operation may be performed to obtain the PPy/NiPcTs film of sensor S6 by biasing the film to a potential ($E_f$) of 0.0 V for 60 s.

The PPy/NiPcTs film of sensor S6 may be grown electrochemically (via chronoamperometry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The PPy/NiPcTs film of sensor S6 may be, for example, deposited on the substrate 405 illustrated in FIG. 4 having conductive metal traces 410, 416 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 416 and then fills the gap between the conductive metal traces 410, 416. Once the PPy/NiPcTs film of sensor S6 has been deposited, the substrate may be removed from the solution, and then washed with acetonitrile.

A masking material may be used to confine the deposition of the PPy/NiPcTs film of sensor S6 to a sensing area on the substrate designated for sensor S6. For example, a glass membrane (or other masking material) with a central opening that defines the sensing area may be provided on the substrate during the deposition of the PPy/NiPcTs film of sensor S6, and then removed. Prior to depositing the PPy/

NiPcTs film of sensor S6, the substrate may be cleaned with acetone, and rinsed with distilled water.

Optionally, prior to depositing the PPy/NiPcTs film of sensor S6, the sensing area may be treated with hexamethyldisilazane (HMDS) or other suitable coupling agent to improve the adhesion of the PPy/NiPcTs film of sensor S6 to the substrate.

Sensor Seven (S7)
Polymer: polyaniline (PANI)
Electrochemical procedure: cyclic voltammetry (CV)
Monomer: analine
Electrolyte: hydrochloric acid (HCl)

Sensor S7 may be obtained from an electrolytic solution of aniline 1.0 mol/L and HCl 2.0 mol/L in deionized water. The chlorine anion ($Cl^-$) serves as a doping anion in sensor S7. The PANI/HCl film of sensor S7 may be grown (i.e., deposited onto a substrate between two separated electrodes) via a cyclic voltommetry (CV) operation. The cyclic voltammetry operation may be performed using 15 repetitive cycles from −0.3 V to 0.9 V at a scan rate of 50 mV/s, followed by a cycle from −0.3 V to a final (conditioning) potential of 0.0 V at a scan rate of 50 mV/s.

The PANI/HCl film of sensor S7 may be grown electrochemically (via cyclic voltommetry) onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The electrodes may be in the form of conductive metal traces deposited on the bottom surface 404 of the printed circuit board substrate 405 using conventional techniques. The PANI/HCl film of sensor S7 may be, for example, deposited on the substrate 405 illustrated in FIG. 4 having conductive metal traces 410, 417 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 417 and then fills the gap between the conductive metal traces 410, 417. Once the PANI/HCl film of sensor S7 has been deposited, the substrate may be removed from the solution, and then washed with acetonitrile.

A masking material may be used to confine the deposition of the PANI/HCl film of sensor S7 to a sensing area on the substrate designated for sensor S7. For example, a glass membrane (or other masking material) with a central opening that defines the sensing area may be provided on the substrate during the deposition of the PANI/HCl film of sensor S7, and then removed. Prior to depositing the PANI/HCl film of sensor S7, the substrate may be cleaned with acetone, and rinsed with distilled water or ultrapure water (UPW).

Optionally, prior to depositing the PANI/HCl film of sensor S7, the sensing area may be treated with hexamethyldisilazane (HMDS) or other suitable coupling agent to improve the adhesion of the PANI/HCl film of sensor S7 to the substrate.

Sensor Eight (S8)
Polymer: polypyrrole (PPy)
Electrochemical procedure: cyclic voltammetry (CV)
Monomer: pyrrole
Electrolyte: tetrasulfonated nickel phthalocyanine (NiPcTs)

Sensor S8 may be obtained from an electrolytic solution of pyrrole 0.1 mol/L and nickel(II) phthalocyanine-tetrasulfonic acid tetrasodium salt (NiPcTs) 0.01 mol/L in deionized water. Anions of nickel phthalocyanine tetrasulfonic acid, such as the tetra-anion $[NiPc]^{4-}$, serve as doping anions in sensor S8. The PPy/NiPcTs film of sensor S8 may be grown (i.e., deposited onto a substrate between two separated electrodes) via a cyclic voltommetry (CV) operation. The cyclic voltammetry operation may be performed using 15 repetitive cycles from −0.3 V to 0.9 V at a scan rate of 50 mV/s, followed by a cycle from −0.3 V to a final (conditioning) potential of 0.0 V at a scan rate of 50 mV/s.

The PPy/NiPcTs film of sensor S8 may be grown electrochemically onto a suitable substrate having suitable electrodes. Suitable substrates include, but are not limited to, glass substrates, alumina substrates, and silicon chip substrates. Suitable electrodes include, but are not limited to, indium tin oxide (ITO) electrodes, gold electrodes, copper electrodes, and silver electrodes. The PPy/NiPcTs film of sensor S8 may be, for example, deposited on the substrate 405 illustrated in FIG. 4 having conductive metal traces 410, 418 separated from each other by a suitable gap (electrode spacing). The electrode spacing may be, for example, 50 μm or 75 μm. One skilled in the art will appreciate, however, that any suitable electrode spacing may be used. The polymeric film grows first on the conductive metal traces 410, 418 and then fills the gap between the conductive metal traces 410, 418. Once the PPy/NiPcTs film of sensor S8 has been deposited, the substrate may be removed from the solution, and then washed with acetonitrile.

A masking material may be used to confine the deposition of the PPy/NiPcTs film of sensor S8 to a sensing area on the substrate designated for sensor S8. For example, a glass membrane (or other masking material) with a central opening that defines the sensing area may be provided on the substrate during the deposition of the PPy/NiPcTs film of sensor S8, and then removed. Prior to depositing the PPy/NiPcTs film of sensor S8, the substrate may be cleaned with acetone, and rinsed with distilled water.

Optionally, prior to depositing the PPy/NiPcTs film of sensor S8, the sensing area may be treated with hexamethyldisilazane (HMDS) or other suitable coupling agent to improve the adhesion of the PPy/NiPcTs film of sensor S8 to the substrate.

Figure 6:
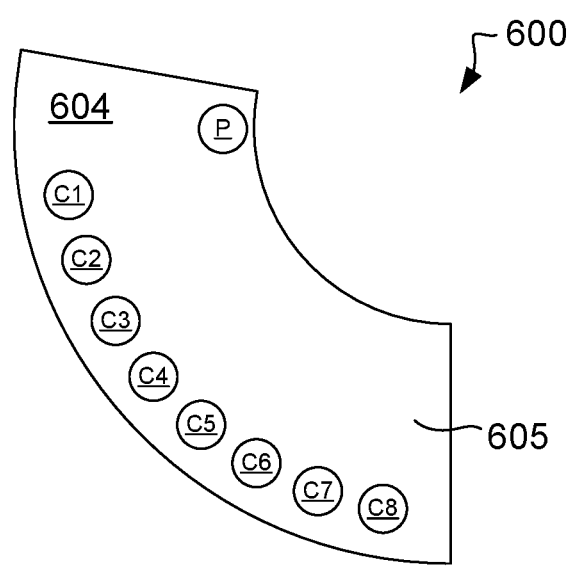
FIG. 6 is a top view of an interrogation probe having a power-out contact and a plurality of sensor-in contacts in the form of conductive pads deposited on a mating surface of printed circuit board substrate, in accordance with some embodiments of the present invention.

FIG. 6 is a top view of an interrogation probe 600 having a power-out contact P and a plurality of sensor-in contacts C1-C8 in the form of conductive pads deposited on a mating surface 604 of a printed circuit board substrate 605, in accordance with some embodiments of the present invention. The interrogation probe 600, which mates with the interrogation interface 500 of FIG. 5 of a quality-sensing bottle cap, is a component of an analytic unit (e.g., 704 in FIG. 7), described below. In accordance with some embodiments, the analytic unit may be used by a consumer to analyze the quality of a liquid, such as olive oil, contained in a bottle sealed with the quality-sensing bottle cap.

The power-out contact P of the interrogation probe 600 is configured to be engaged with the power-in contact P of the interrogation interface 500 of FIG. 5. Likewise, the sensor-in contacts C1-C8 of the interrogation probe 600 are respectively configured to be engaged with the sensor-out contacts C1-C8 of the interrogation probe 500 of FIG. 5. In essence, the physical layout of the interrogation probe 600 of FIG. 6 is the mirror image of the interrogation interface 500 of FIG. 5.

In accordance with some embodiments, a keying structure may be used to facilitate engagement between the conductive pads of the interrogation probe 600 and the conductive pads of the interrogation interface 500. Such a keying structure may, for example, include one or more protrusions on the interrogation probe 600 that cooperate with one or more notches on the interrogation interface 500.

Figure 7:
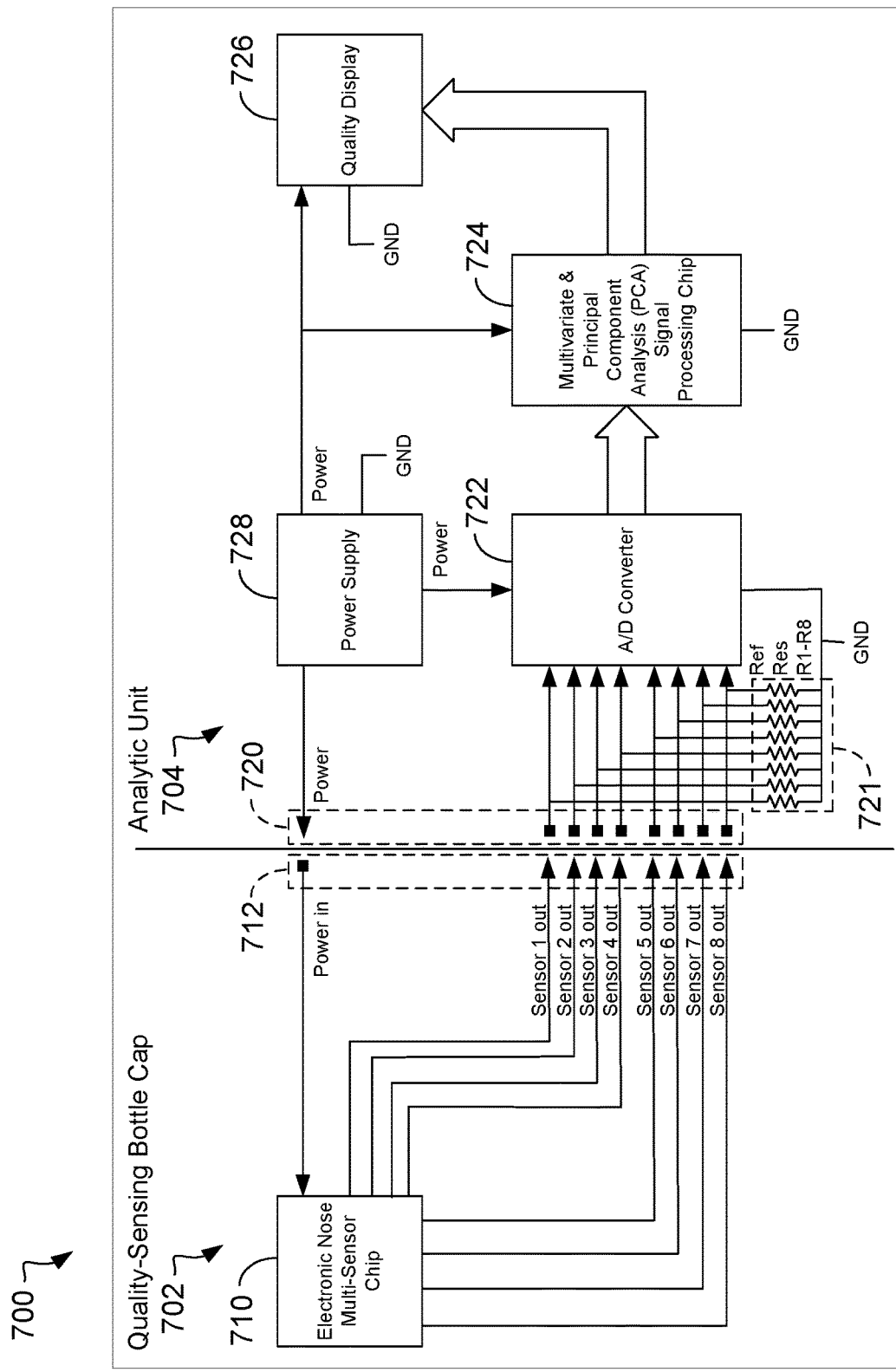
FIG. 7 is a block diagram illustrating an electronic nose system that employs a quality-sensing bottle cap and an analytic unit, in accordance with some embodiments of the present invention.

FIG. 7 is a block diagram illustrating an electronic nose system 700 that employs a quality-sensing bottle cap 702 and an analytic unit 704, in accordance with some embodiments of the present invention. The quality-sensing bottle cap 702 includes an electronic nose multi-sensor chip 710 operatively connected to an interrogation interface 712 by a power-in line (denoted in FIG. 7 as "Power in") and eight sensor-out lines (denoted in FIG. 7 as "Sensor 1 out," "Sensor 2 out," . . . "Sensor 8 out"). The electronic nose multi-sensor chip 710 of FIG. 7 may, for example, correspond to the sensor array 400 of FIG. 4 having eight conductive polymeric sensors S1-S8. Likewise, the interrogation interface 712 of FIG. 7 may correspond to the interrogation interface 500 of FIG. 5. The electronic nose multi-sensor chip 710 and the interrogation interface 712 may be disposed on opposite sides of the same printed circuit board substrate, analogous to the sensor array 400 of FIG. 4 and interrogation interface 500 of FIG. 5 being disposed on opposite sides of the printed circuit board substrate 405 of FIGS. 4 and 5. One skilled in the art will appreciate, however, that the electronic nose multi-sensor chip 710 and the interrogation interface 712 may be disposed on separate elements of the quality-sensing bottle cap 702.

The analytic unit 704 includes an interrogation probe 720, a reference resistor bank 721, an analog-to-digital converter 722, a multivariate and principle component analysis (PCA) signal processing chip 724, a display 726, and a power supply 728 for providing electric power to elements of the analytic unit 704 as well as to the electronic nose multi-sensor chip 710 of the quality-sensing bottle cap 702.

The interrogation probe 720 of the analytic unit 704 includes conductive pads configured to engage with the conductive pads of the interrogation interface 712 of the quality sensing unit 702. The interrogation probe 720 of FIG. 7 may, for example, correspond to the interrogation probe 600 of FIG. 6.

The power supply 728 is electrically connected to the interrogation probe 712 by a power-out line. The power-out line is electrically connected (via engagement between the interrogation probe 720 and the interrogation interface 712) to the power-in line of the quality-sensing bottle cap 702 (denoted in FIG. 7 as "Power in"). The power supply 728 provides an electrical voltage/current through each of the conductive polymeric sensors (e.g., S1-S8 in FIG. 4) of the electronic nose multi-sensor chip 710. For example, referring turning temporarily back to FIGS. 4-6, the current provided by the power supply 728 flows through the power-out contact P of the interrogation probe 600 (FIG. 6), the power-in contact P of the interrogation interface 500 (FIG. 5), the plated through-hole via 420 (FIG. 4), the conductive metal trace 410 (FIG. 4), the eight conductive polymer traces that respectively define the eight conductive polymeric sensors S1-S8 (FIG. 4), the eight conductive metal traces 411-418 (FIG. 4), the eight plated through-hole vias 421-428 (FIG. 4), the eight sensor-out contacts C1-C8 of the interrogation interface 500 (FIG. 5), and the eight sensor-in contacts C1-C8 of the interrogation probe 600 (FIG. 6).

The analog-to-digital converter 722 is electrically connected, in conjunction with the reference resistor bank 721, to the interrogation probe 720 by eight sensor-in lines. The reference resistor bank 721 includes eight reference resistors R1-R8 each respectively connected to a corresponding one of the eight sensor-in lines. The eight sensor-in lines are respectively electrically connected (via engagement between the interrogation probe 720 and the interrogation interface 712) to the eight sensor-out lines of the quality-sensing bottle cap 702 (denoted in FIG. 7 as "Sensor 1 out," "Sensor 2 out," . . . "Sensor 8 out"). The eight reference resistors R1-R8 serve as voltage dividers with respect to the eight conductive polymeric sensors (e.g., S1-S8 of FIG. 4) of the electric nose multi-sensor chip 710. The analog-to-digital converter 722 senses any drop and/or increase in the voltage across each of the eight reference resistors R1-R8 that results from changes in the impedance of the eight conductive polymer sensors of the electric nose multi-sensor chip 710 upon exposure of the eight conductive polymeric sensors to volatile organic components (VOCs) in a headspace above a liquid contained in a bottle sealed with the quality-sensing bottle cap 702. Each of the reference resistors R1-R8 may, for example, have an identical electrical impedance. The analog-to-digital converter 722 converts the sensor output from each of the eight conductive polymeric sensors of the electronic nose multi-sensor chip 710 to digital data and outputs the digital data to the multivariate and PCA signal processing chip 724.

The analog-to-digital converter 722 may, for example, use the sensed voltage across each of the eight reference resistors R1-R8, along with the known value of the voltage provided by the power supply 728 to each of the eight conductive polymeric sensors of the electric nose multi-sensor chip 710 and the known value of the resistance of each of the eight reference resistors R1-R8, to measure the resistance of each of the eight conductive polymeric sensors. The resistance $R_S$ of a particular one of the conductive polymeric sensors (S1-S8) is given by the formula $R_S=[(V_1-V_2)/V_2]\times R_R$, wherein $V_1$ is the known voltage of the power supply 728 to each of the conductive polymeric sensors (S1-S8), $V_2$ is the sensed voltage across the corresponding reference resistor (R1-R8), and $R_R$ is the known resistance of the corresponding reference resistor (R1-R8).

In accordance with some embodiments, the analog-to-digital converter 722 may output as digital data to the multivariate and PCA signal processing chip 724, the peak value of percentage variation of resistance $[(R-R_0)/R_0]\times 100$ of each sensor exposed to volatile organic components (VOCs) in a headspace of a liquid contained in a bottle sealed with the quality-sensing bottle cap 702. R is the measured resistance (at peak value) of a particular sensor after exposure. $R_0$ is the original resistance of the particular sensor before exposure.

Figure 10:
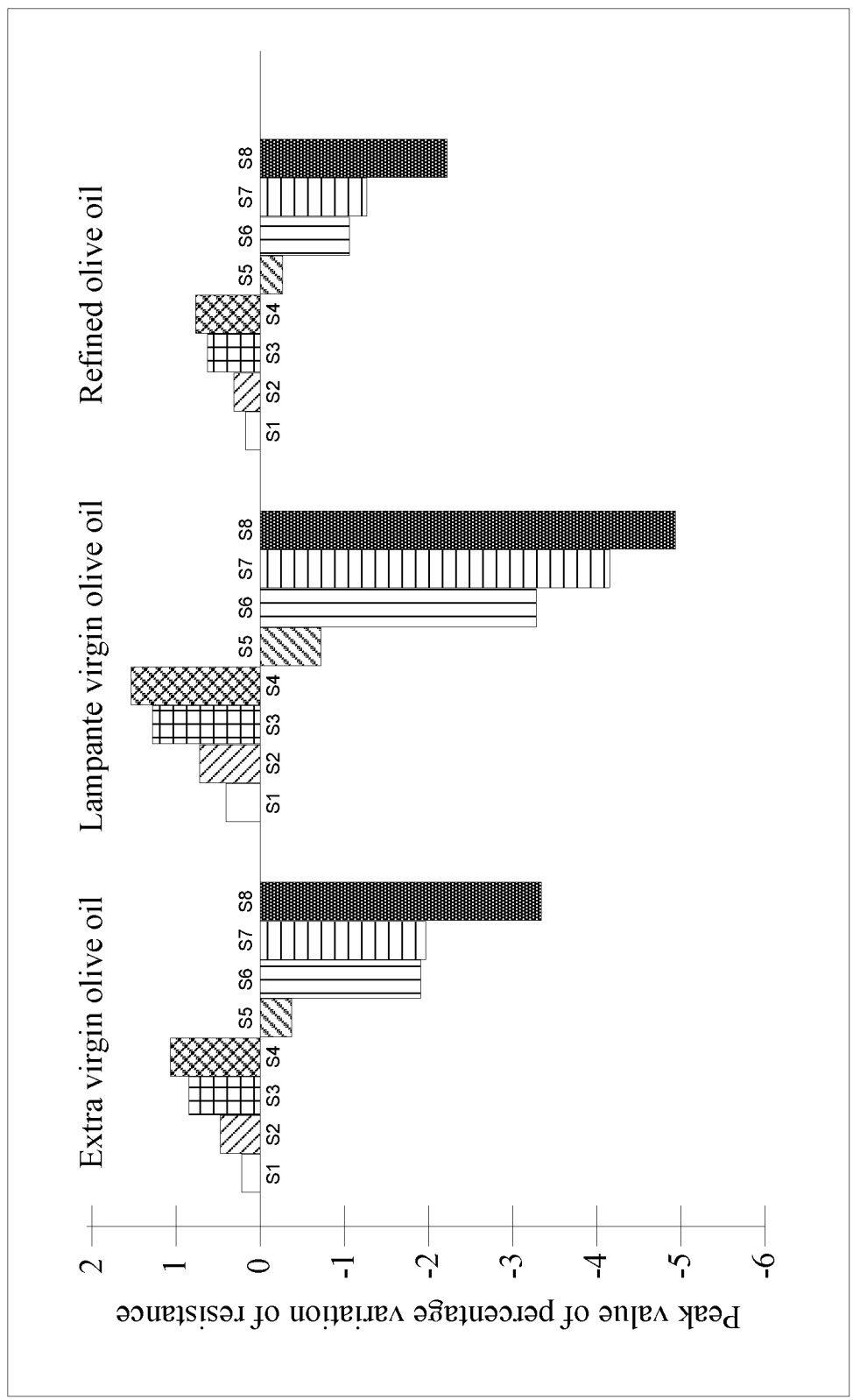
FIG. 10 is a bar graph illustrating a prophetic example of the peak value of percentage variation of resistance obtained by each of eight conductive polymeric sensors of a sensor array exposed to a headspace above each of three different types of olive oil (i.e., extra virgin olive oil, lampante virgin olive oil, and refined olive oil) contained in the same or identical bottle(s) sealed with the same or identical quality-sensing bottle cap(s), in accordance with some embodiments of the present invention.
Figure 12:
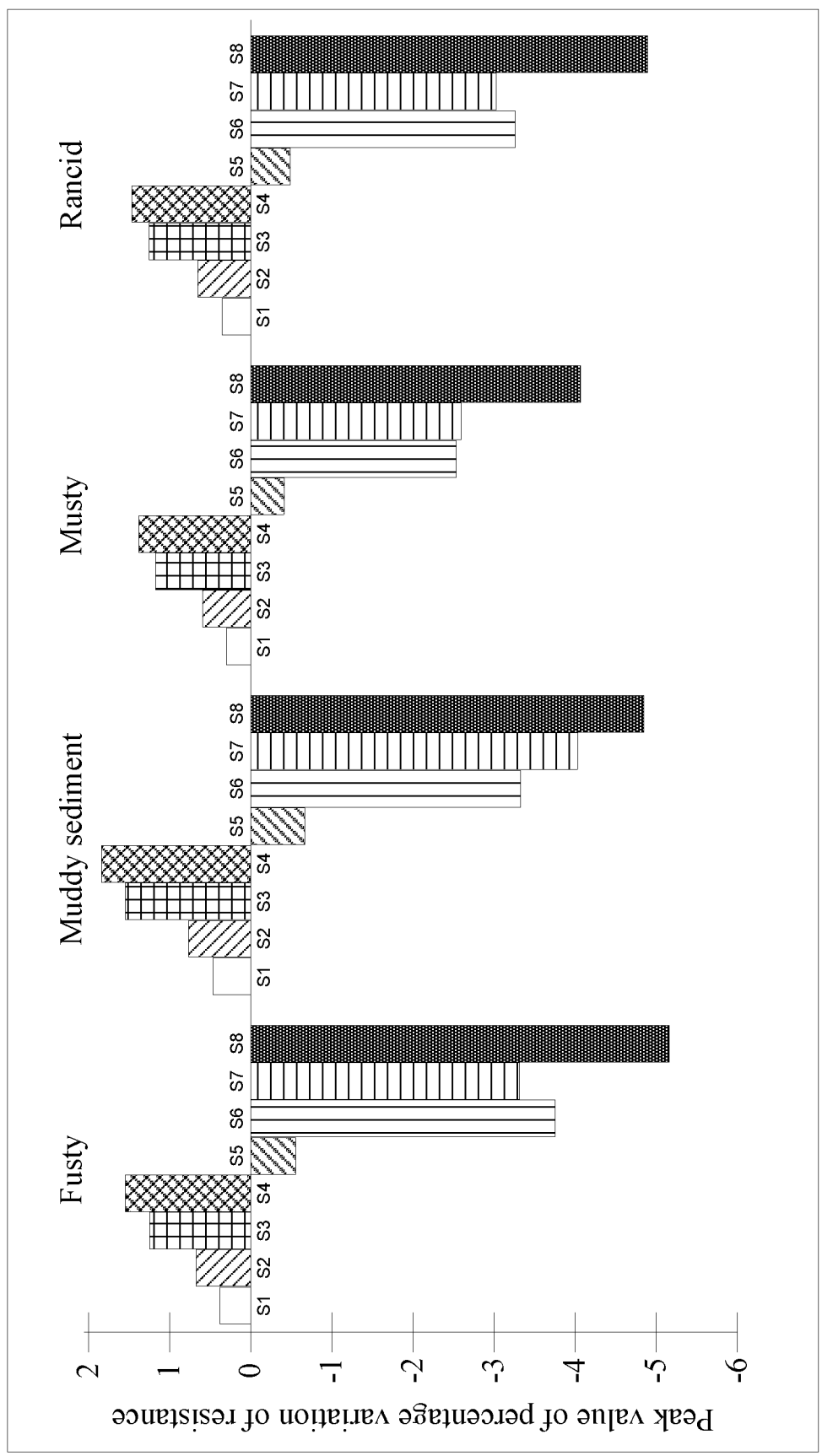
FIG. 12 is a bar graph illustrating a prophetic example of the peak value of percentage variation of resistance obtained by each of eight conductive polymeric sensors of a sensor array exposed to a headspace above each of four negative-attribute olive oils (i.e., fusty, muddy sediment, musty, and rancid) contained in the same or identical bottle(s) sealed with the same or identical quality-sensing bottle cap(s), in accordance with some embodiments of the present invention.

The peak value of percentage variation of resistance may be presented as a bar graph. The bar graph provides what is essentially the sensor array's response "fingerprint" for each of the one or more particular liquids. As one example, FIG. 10 is a bar graph illustrating a prophetic example of the peak value of percentage variation of resistance obtained by each of eight conductive polymeric sensors (S1-S8) of a sensor array exposed to a headspace above each of three different types of olive oil (i.e., extra virgin olive oil, lampante virgin olive oil, and refined olive oil) contained in the same or identical bottle(s) sealed with the same or identical quality-sensing bottle cap(s), in accordance with some embodiments of the present invention. As another example, FIG. 12 is a bar graph illustrating a prophetic example of the peak value of percentage variation of resistance obtained by each of eight conductive polymeric sensors (S1-S8) of a sensor array exposed to a headspace above each of four different negative attribute olive oils (i.e., fusty, muddy sediment, musty, and rancid) contained in the same or identical bottle(s) sealed with the same or identical quality-sensing bottle cap(s), in accordance with some embodiments of the present invention.

The multivariate and PCA signal processing chip 724 receives the digital data from the analog-to-digital converter 722, analyzes the digital data along with reference data using a multivariate statistical technique to determine a quality classification of the liquid contained in the bottle. The reference data is associated with one or more liquids each of known quality classification. Principal component analysis, for example, may be used by the multivariate and PCA signal processing chip 724 to calculate a first principle component and a second principle component of the digital data and the reference data.

In some embodiments, the multivariate and PCA signal processing chip 724 may analyze the digital data associated with a liquid purported to be extra virgin olive oil along with reference data associated with different types of olive oil using PCA to calculate a first principle component and a second principle component of the digital data and the reference data. For example, FIG. 11 is a plot illustrating a prophetic example of the first principal component and the second principal component resulting from a PCA of the response of a sensor array exposed to a headspace above a liquid purported to be extra virgin olive oil contained in a bottle sealed with a quality-sensing bottle cap, in accordance with some embodiments of the present invention, and the responses of a sensor array exposed to a headspace above each of three different types of olive oil (i.e., extra virgin olive oil, lampante virgin olive oil, and refined olive oil) contained in the same or identical bottle(s) sealed with the same or identical quality-sensing bottle cap(s).

Figure 11:
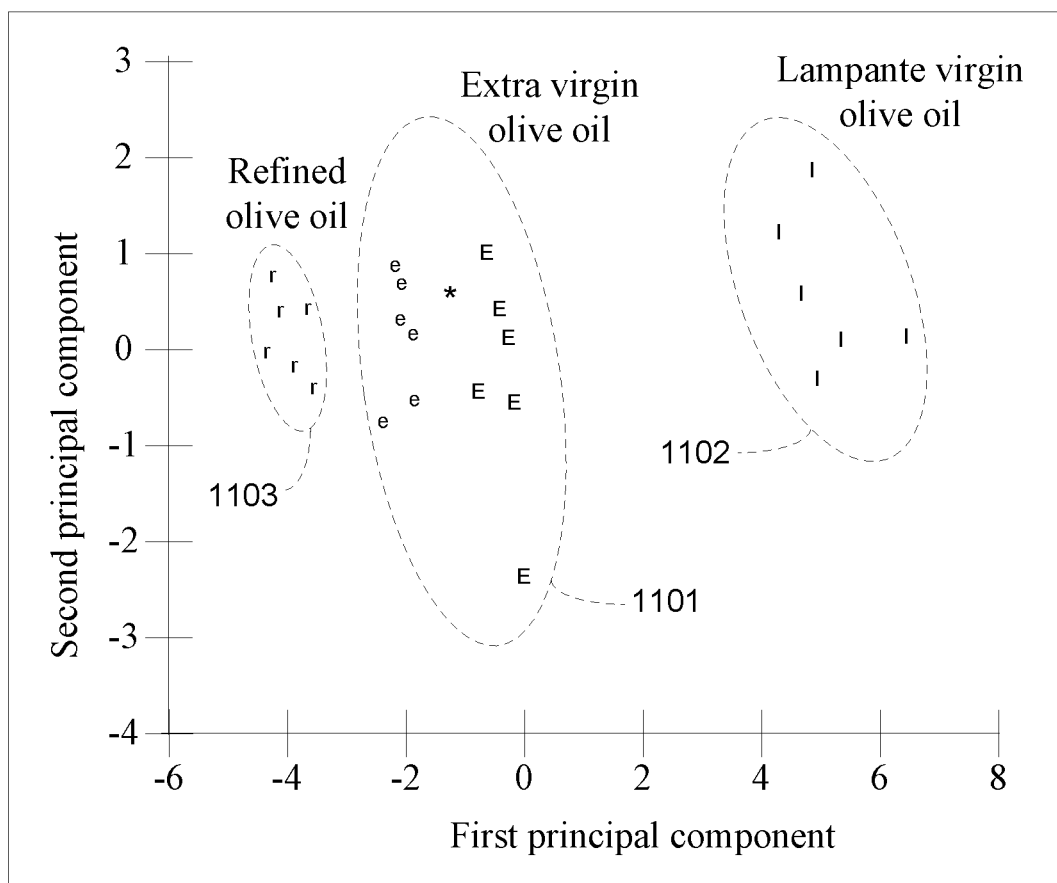
FIG. 11 is a plot illustrating a prophetic example of the first principal component and the second principal component resulting from a principal component analysis (PCA) of the response of a sensor array exposed to a headspace above a liquid purported to be extra virgin olive oil contained in a bottle sealed with a quality-sensing bottle cap, in accordance with some embodiments of the present invention, and the responses of a sensor array exposed to a headspace above each of three different types of olive oil (i.e., extra virgin olive oil, lampante virgin olive oil, and refined olive oil) contained in the same or identical bottle(s) sealed with the same or identical quality-sensing bottle cap(s).

In FIG. 11, the first principle component and the second principle component resulting from the PCA of the sensor array's response to six repeated exposures to each of two different extra virgin olive oil are each respectively plotted as "e" and "E" within a cluster 1101 ("Extra virgin olive oil"), six repeated exposures to lampante virgin olive oil are each plotted as "l" within a cluster 1102 ("Lampante virgin olive oil"), and six repeated exposures to refined olive oil are each plotted as "r" within a cluster 1103 ("Refined olive oil"). Also in FIG. 11, the first principle component and the second principle component resulting from the PCA of the sensor array's response to a single exposure to the liquid purported to be extra virgin olive oil is plotted as "*", which in this particular case happens to fall within the "Extra virgin olive oil" cluster 1101. In this particular case, because the plotted "*" falls within the "Extra virgin olive oil" cluster 1101, the multivariate and PCA signal processing chip 724 may, for example, cause the display 726 to indicate that the liquid is indeed extra virgin olive oil. In cases where the plotted "*" falls within the "Lampante virgin olive oil" cluster 1102 or the "Refined olive oil" cluster 1103, the multivariate and PCA signal processing chip 724 may, for example, cause the display 726 to indicate that the liquid is not extra virgin olive oil, but rather lampante virgin olive oil or refined olive oil. In cases where the plotted "*" falls outside any of the clusters 1101-1103, the multivariate and PCA signal processing chip 724 may, for example, cause the display 726 to indicate that the liquid is not extra virgin olive oil.

Figure 13:
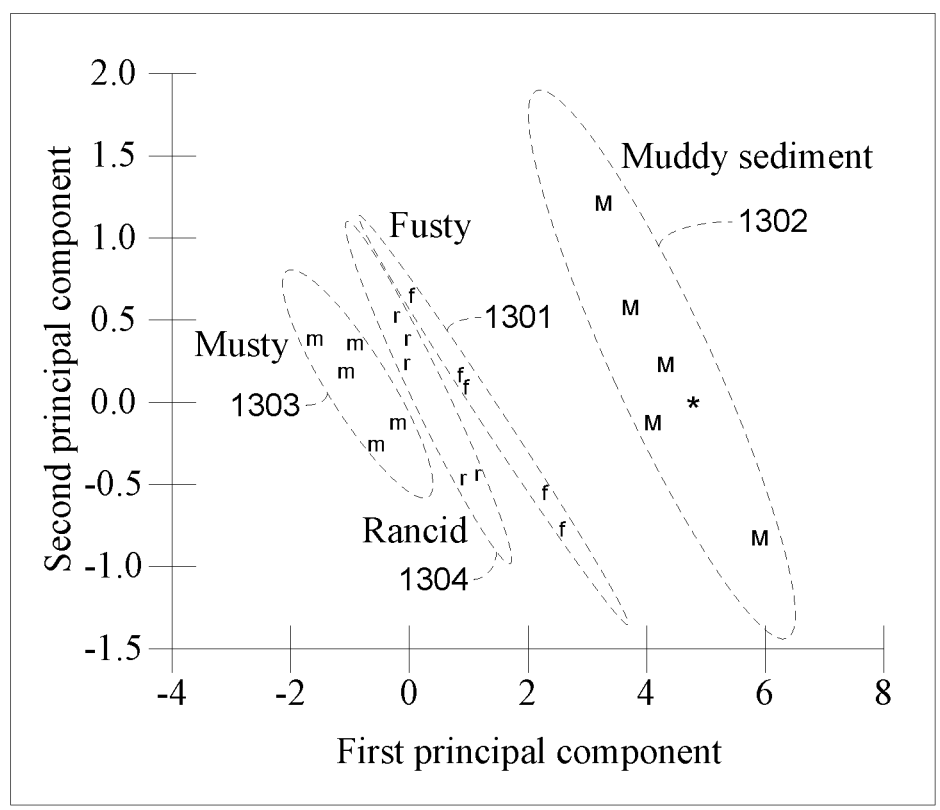
FIG. 13 is a plot illustrating a prophetic example of the first principal component and the second principal component resulting from a principal component analysis (PCA) of the response to a sensor array exposed to a headspace above a liquid purported to be olive oil contained in a bottle sealed with a quality-sensing bottle cap, and the responses to a sensor array exposed to a headspace above each four different negative-attribute olive oils (i.e., fusty, muddy sediment, musty, and rancid) contained in the same or identical bottle(s) sealed with the same or identical quality-sensing bottle cap(s).

In some embodiments, the multivariate and PCA signal processing chip 724 may analyze the digital data associated with a liquid purported to be olive oil along with reference data associated with different negative-attribute olive oils using PCA to calculate a first principle component and a second principle component of the digital data and the reference data. FIG. 13 is a plot illustrating a prophetic example of the first principal component and the second principal component resulting from a PCA of the response to a sensor array exposed to a headspace above a liquid purported to be olive oil contained in a bottle sealed with a quality-sensing bottle cap, and the responses to a sensor array exposed to a headspace above each four different negative-attribute olive oils (i.e., fusty, muddy sediment, musty, and rancid) contained in the same or identical bottle(s) sealed with the same or identical quality-sensing bottle cap(s).

In FIG. 13, the first principle component and the second principle component resulting from the PCA of the sensor array's response to five repeated exposures to olive oil identified as having the fusty negative-attribute are each plotted as "f" within a cluster 1301 ("Fusty"), five repeated exposures to olive oil identified as having the muddy sediment negative-attribute are each plotted as "M" within a cluster 1302 ("Muddy sediment"), five repeated exposures to olive oil identified as having the musty negative-attribute are each plotted as "m" within a cluster 1303 ("Musty"), and five repeated exposures to olive oil identified as having the rancid negative-attribute are each plotted as "r" within a cluster 1304 ("Rancid"). Also in FIG. 13, the first principle component and the second principle component resulting from the PCA of the sensor array's response to a single exposure to the liquid purported to be olive oil is plotted as "*", which in this particular case happens to fall within the "Muddy sediment" cluster 1302. In this particular case, because the plotted "*" falls within the "Muddy sediment" cluster 1302, the multivariate and PCA signal processing chip 724 may, for example, cause the display 726 to indicate that the liquid is olive oil but has the muddy sediment negative-attribute. In cases where the plotted "*" falls within the "Fusty" cluster 1301, the "Musty" cluster 1303, or the "Rancid" cluster 1304, the multivariate and PCA signal processing chip 724 may, for example, cause the display 726 to indicate that the liquid is olive oil, but has the applicable (i.e., fusty, musty, or rancid) negative-attribute. In cases where the plotted "*" falls outside any of the clusters 1301-1304, the multivariate and PCA signal processing chip 724 may, for example, cause the display 726 to indicate that the verification is indeterminate with respect to the negative-attributes.

The display 726, which is operatively connected to the multivariate and PCA signal processing chip 724, may be used for displaying quality verification results.

Figure 8:
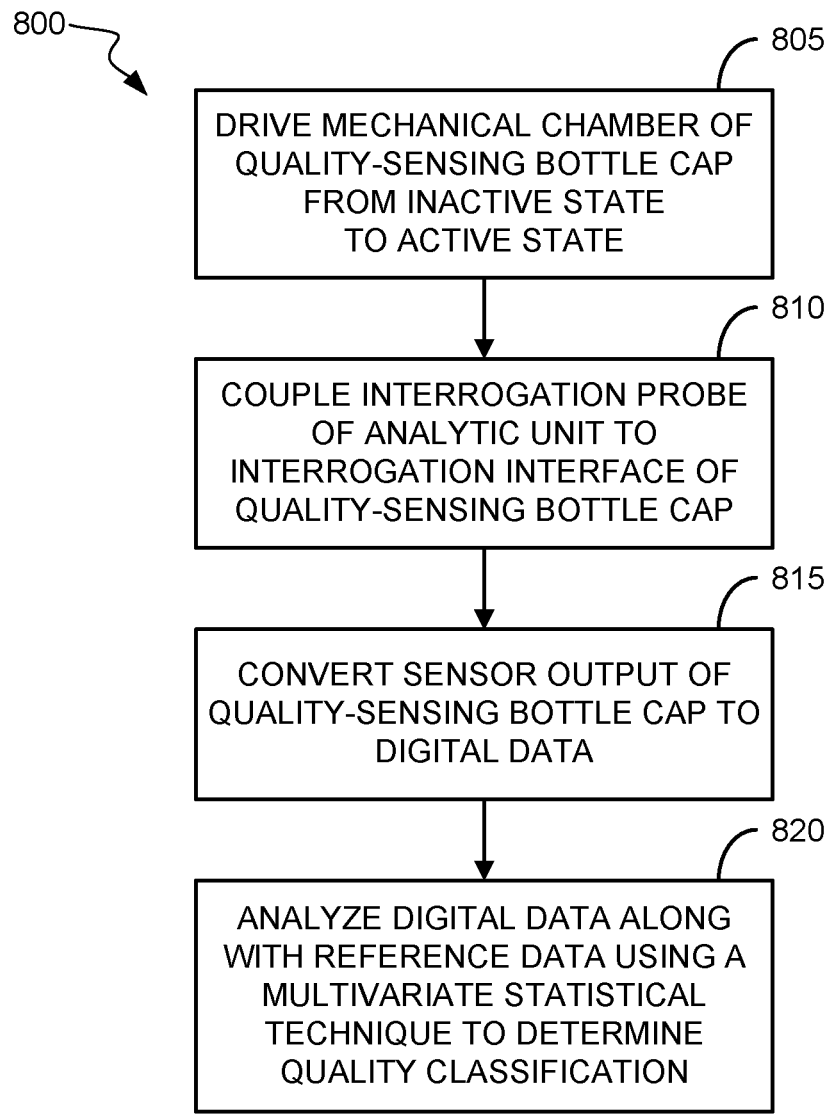
FIG. 8 is flow diagram illustrating a method of analyzing a headspace above a liquid contained in a bottle sealed with a quality-sensing bottle cap, according to some embodiments of the present invention.

FIG. 8 illustrates a flow diagram of a method 800 of analyzing a headspace above a liquid, such as extra virgin olive oil, contained in a bottle sealed with a quality-sensing bottle cap, according to some embodiments of the present invention. In the method 800, the steps discussed below (steps 805-820) are performed. These steps are set forth in their preferred order. It must be understood, however, that the various steps may occur at different times relative to one another than shown, or may occur simultaneously. Moreover, those skilled in the art will appreciate that one or more of the steps may be omitted.

The method 800 begins by driving a mechanical chamber of the quality-sensing bottle cap from an inactive state to an active state (step 805). For example, the quality-sensing bottle cap may be pressed down (e.g., by a consumer on a store shelf) to cause a protruding element to pierce a septum. This step may be accomplished, in accordance with some embodiments of the present invention, either by pressing down on an overcap ring (prior to twisting off the quality-sensing bottle cap using a "press down and twist" safety cap mechanism) or by pressing down on a bump-out area of a top lid seal.

The method 800 continues by coupling an interrogation probe of an analytic unit to an interrogation interface of the quality-sensing bottle cap to obtain a sensor output from each of a plurality of conductive polymeric sensors of a sensor array of the quality-sensing bottle cap (step 810). The sensor output from each of the conductive polymeric sensors may, for example, be representative of electrical impedance of that particular conductive polymeric sensor. This step may be accomplished, in accordance with some embodiments of the present invention, by engaging a power-out contact exposed on the interrogation probe against a power-in contact exposed on the quality-sensing bottle cap, wherein the power-in contact is in electrical communication with a first side of all of the conductive polymeric sensors, and by engaging a plurality of sensor-in contacts exposed on the interrogation probe against a plurality sensor-out contacts exposed on the quality-sensing bottle cap, wherein each of the plurality of sensor-out contacts is in electrical communication with a second side of a respective one of the conductive polymeric sensors.

The method 800 continues by converting the sensor output from each of the conductive polymeric sensors to digital data (step 815). This step may be accomplished, in accordance with some embodiments of the present invention, by utilizing an analog-to-digital converter and a bank of reference resistors. The analog-to-digital converter may, for example, use the sensed voltage across each of the reference resistors, along with the known value of the voltage provided by the power supplied to each of the plurality of conductive polymeric sensors and the known value of the resistance of each of the reference resistors, to measure the resistance of each of the plurality of conductive polymeric sensors.

The method 800 continues by analyzing the digital data along with reference data using a multivariate statistical technique to determine a quality classification of the liquid contained in the bottle (step 820). This step may be accomplished, in accordance with some embodiments of the present invention, by using PCA to calculate a first principle component and a second principle component of the digital data and the reference data. The reference data is associated with one or more reference liquids each of known quality classification.

For example, in embodiments where the liquid contained in the bottle is to be verified as olive oil of a particular classification, the reference data may be associated with the one or more olive oils each of a known quality classification (e.g., refined olive oils, extra virgin olive oils, and lampante olive oils). In embodiments where the liquid in the bottle is to be verified as olive oil with the presence or absence of negative attributes, the reference data may be associated with one or more olive oils each with a known negative attribute (e.g., "fusty" olive oils, "muddy sediment" olive oils, "musty" olive oils, and "rancid" olive oils).

The reference data may be obtained, for example, by using an electronic nose system to first analyze the reference liquids. For example, sensor output from each of a plurality of conductive polymeric sensors of a sensor array (the same or identical to that of the quality-sensing bottle cap) in response to being exposed to the headspace above each of the reference liquids may be converted to digital data using an analog-to-digital converter and stored for later use as the reference data.

Figure 9:
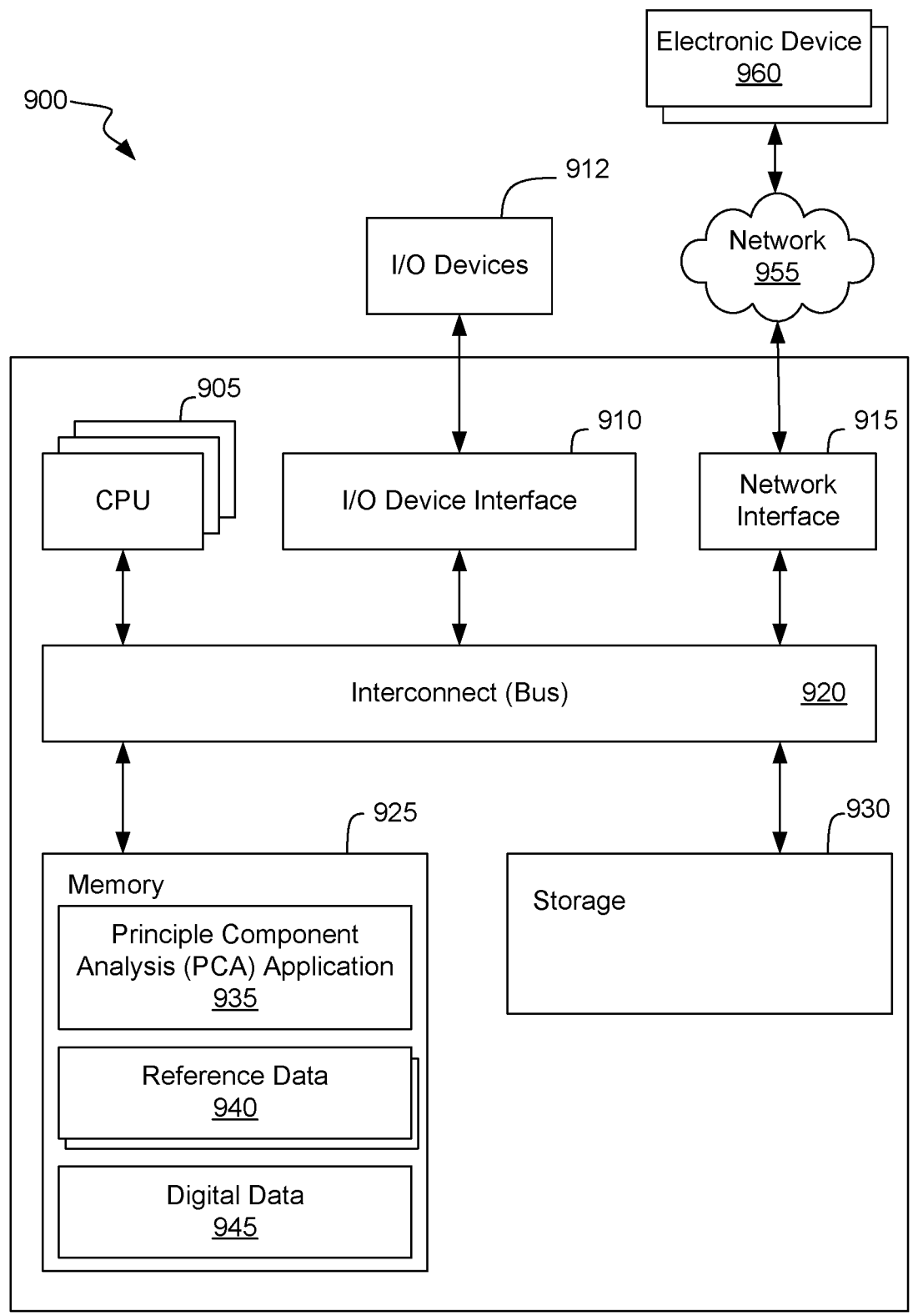
FIG. 9 is a block diagram illustrating an exemplary representation of a computer system for performing a computer-implemented method for verifying the quality of a liquid contained in a bottle sealed with a quality-sensing bottle cap, in accordance with some embodiments of the present invention.

FIG. 9 illustrates an exemplary representation of a computer system 900 for performing a computer-implemented method for verifying the quality of a liquid contained in a bottle sealed with a quality-sensing bottle cap, in accordance with some embodiments of the present invention. For the purposes of this disclosure, computer system 900 may represent practically any type of computer, computer system, or other programmable electronic device, including but not limited to, a client computer, a server computer, a portable computer, a handheld computer, an embedded controller, etc. In some embodiments, computer system 900 may be implemented using one or more networked computers, e.g., in a cluster or other distributed computing system.

The computer system 900 may include, without limitation, one or more processors (CPUs) 905, a network interface 915, an interconnect 920, a memory 925, and storage 930. The computer system 900 may also include an I/O device interface 910 used to connect I/O devices 912, e.g., keyboard, display, and mouse devices, to the computer system 900.

In addition, the I/O device interface 910 may also be used to connect I/O devices such as a quality-sensing bottle cap, in accordance with some embodiments of the present invention. For example, referring temporarily back to FIG. 7, to enable connection to the quality-sensing bottle cap 702, the I/O device interface 910 may include components corresponding to the interrogation probe 720, the bank of resistors 721, and the analog-to-digital converter 722.

Each processor 905 may retrieve and execute programming instructions stored in the memory 925 or storage 930. Similarly, the processor 905 may store and retrieve application data residing in the memory 925. The interconnect 920 may transmit programming instructions and application data between each processor 905, I/O device interface 910, network interface 915, memory 925, and storage 930. The interconnect 920 may be one or more busses. The processor 905 may be a single central processing unit (CPU), multiple CPUs, or a single CPU having multiple processing cores in various embodiments. In one embodiment, a processor 905 may be a digital signal processor (DSP).

The memory 925 may be representative of a random access memory, e.g., Static Random Access Memory (SRAM), Dynamic Random Access Memory (DRAM), read-only memory, or flash memory. The storage 930 may be representative of a non-volatile memory, such as a hard disk drive, solid state device (SSD), or removable memory cards, optical storage, flash memory devices, network attached storage (NAS), or connections to storage area network (SAN) devices, or other devices that may store non-volatile data. The network interface 915 may be configured to transmit data via the communications network 955.

The memory 925 may include a PCA application 935 and one or more data files denoted in FIG. 9 as "Reference Data 940" and "Digital Data 945". Although these elements are illustrated as residing in the memory 925, any of the elements, or combinations thereof, may reside in the storage 930 or partially in the memory 925 and partially in the storage 930. The one or more data files (e.g., reference data 940) may also reside, at least partially, in a data base (not shown) which the computer system 900 may access through the network 955. The reference data 940 and the digital data 945 of FIG. 9 may, for example, correspond to the reference data and the digital data described above with respect to the method 800 of FIG. 8. The PCA application 935 may, for example, be a conventional PCA application such as the PCA in MATLAB, available from The MathWorks, Inc. The PCA application 935 has a set (at least one) of program modules that, in conjunction with the one or more data files 940,941 and a quality-sensing bottle cap (e.g., 702 in FIG. 7), generally carry out the functions and/or methodologies of embodiments of the invention as described herein.

The network 955 may be any suitable network or combination of networks and may support any appropriate protocol suitable for communication of data and/or code to/from the computer system 900 and the electronic device 960. In some embodiments, the network 955 may support wireless communications. In other embodiments, the network 955 may support hardwired communications. The network 955 may be the Internet and may support Internet Protocol in some embodiments. In other embodiments, the network 955 may be implemented as a local area network (LAN) or a wide area network (WAN). The network 955 may also be implemented as a cellular data network. Although the network 955 is shown as a single network in the figures, one or more networks of the same or different types may be included.

As shown, there may be one or more electronic devices 960 connected to the computer system 900 via the network 955. The electronic device 960 may include some or all of the hardware and software elements of the computer system 900 previously described. For the purposes of this disclosure, the electronic device 960 may represent practically any type of computer, computer system, or other programmable electronic device, including but not limited to, a client computer, a server computer, a portable computer, a handheld computer, an embedded controller, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

One skilled in the art will appreciate that many variations are possible within the scope of the present invention. Thus, while the present invention has been particularly shown and described with reference to preferred embodiments thereof, it will be understood by those skilled in the art that these and other changes in form and details may be made therein without departing from the spirit and scope of the present invention.

What is claimed is:

1. A quality-sensing bottle cap, comprising:
   a mechanical chamber configured, in an inactive state, to be closed off from a headspace above a liquid contained in a bottle that is to be sealed with the quality-sensing bottle cap and configured, in an active state, to be open to the headspace;
   a sensor array that includes a plurality of conductive polymeric sensors each exposed within the mechanical chamber;
   an interrogation interface in electrical communication with each of the conductive polymeric sensors;
   an overcap ring, wherein the overcap ring includes a horizontal portion and a vertical portion, and wherein the vertical portion of the overcap ring includes a plurality of projections that selectively engage a sawtooth engagement surface of a threaded ring that includes screw-on threads configured to mate with screw-on threads formed on an upper portion of the bottle;
   a top seal lid, wherein the top seal lid is circular and includes an upper surface and a lower surface, and wherein the top seal lid is configured to be received in the overcap ring such that a peripheral portion of the upper surface of the top seal lid engages the horizontal portion of the overcap ring; and
   a main bottle seal lid, wherein the main bottle seal lid is circular and includes a top side and an underside, wherein the main bottle seal lid is configured to be received in the overcap ring between the top seal lid and the upper portion of the bottle, wherein the underside of the main bottle seal lid includes a sealing ring configured to engage the upper portion of the bottle to seal the bottle, and wherein the mechanical chamber is defined between the lower surface of the top seal lid and the top side of the main bottle seal lid.

2. The quality-sensing bottle cap as recited in claim 1, wherein the main bottle seal lid includes a septum that separates the mechanical chamber from the headspace in the inactive state, and wherein the top seal lid includes a protruding element configured to be capable of piercing the septum to drive the mechanical chamber from the inactive state to the active state.

3. The quality-sensing bottle cap as recited in claim 2, wherein the septum is an elastomeric self-sealing septum.

4. The quality-sensing bottle cap as recited in claim 1, wherein the interrogation interface includes a plurality of contacts on the upper surface of the top seal lid, wherein one of the plurality of contacts is a power-in contact in electrical communication with a first side of all of the conductive polymeric sensors, and wherein the balance of the plurality of contacts are sensor-out contacts each in electrical communication with a second side of a respective one of the conductive polymeric sensors.

5. A method of analyzing a headspace above a liquid contained in a bottle sealed with a quality-sensing bottle cap, wherein the quality-sensing bottle cap comprises: a mechanical chamber configured, in an inactive state, to be closed off from the headspace and configured, in an active state, to be open to the headspace; a sensor array that includes a plurality of conductive polymeric sensors each exposed within the mechanical chamber; and an interrogation interface in electrical communication with each of the conductive polymeric sensors, wherein the interrogation interface includes a plurality of contacts exposed on an outside surface of the quality-sensing bottle cap, wherein one of the plurality of contacts is a power-in contact in electrical communication with a first side of all of the conductive polymeric sensors, and wherein the balance of the plurality of contacts are sensor-out contacts each in electrical communication with a second side of a respective one of the conductive polymeric sensors, the method comprising:
   driving the mechanical chamber from the inactive state to the active state;
   coupling an interrogation probe to the interrogation interface by moving the interrogation probe into electrical engagement with the plurality of contacts to obtain a sensor output from each of the conductive polymeric sensors, wherein the sensor output from each of the conductive polymeric sensors is representative of electrical impedance of that particular conductive polymeric sensor;
   converting the sensor output from each of the conductive polymeric sensors to digital data; and
   analyzing the digital data along with reference data using a multivariate statistical technique to determine a quality classification of the liquid contained in the bottle, wherein the reference data is associated with one or more liquids each of known quality classification.

6. The method as recited in claim 5, wherein the mechanical chamber includes a septum that separates the mechanical chamber from the headspace in the inactive state, and wherein driving the mechanical chamber from the inactive state to the active state includes pressing down the quality-sensing bottle cap to cause a protruding element to pierce the septum.

7. The method as recited in claim 5, wherein coupling an interrogation probe to the interrogation interface by moving the interrogation probe into electrical engagement with the plurality of contacts to obtain a sensor output from each of the conductive polymeric sensors includes:

engaging a power contact exposed on the interrogation probe against the power-in contact exposed on the outside surface of the quality-sensing bottle cap; and engaging a plurality of sensor-in contacts exposed on the interrogation probe against the plurality sensor-out contacts exposed on the outside surface of the quality-sensing bottle cap.

8. The method as recited in claim 5, wherein analyzing the digital data along with reference data using a multivariate statistical technique to determine a quality classification of the liquid contained in the bottle includes using principal component analysis (PCA) to calculate a first principle component and a second principle component of the digital data and the reference data.

9. The method as recited in claim 5, wherein the liquid contained in the bottle is purported to be olive oil, and wherein the one or more liquids each of known quality classification is/are selected from the group consisting of refined olive oils, extra virgin olive oils, lampante olive oils, and combinations thereof.

10. The method as recited in claim 5, wherein the liquid contained in the bottle is purported to be olive oil, and wherein the one or more liquids each of known quality classification is/are selected from the group consisting of "fusty" olive oils, "muddy sediment" olive oils, "musty" olive oils, "rancid" olive oils, and combinations thereof.

11. An electronic nose system, comprising:

a bottle containing a liquid and sealed with a quality-sensing bottle cap, wherein the quality-sensing bottle cap comprises: a mechanical chamber configured, in an inactive state, to be closed off from a headspace above the liquid contained in the bottle and configured, in an active state, to be open to the headspace; a sensor array that includes a plurality of conductive polymeric sensors each exposed within the mechanical chamber; and an interrogation interface in electrical communication with each of the conductive polymeric sensors, wherein the interrogation interface includes a plurality of contacts exposed on an outside surface of the quality-sensing bottle cap, wherein one of the plurality of contacts is a power-in contact in electrical communication with a first side of all of the conductive polymeric sensors, and wherein the balance of the plurality of contacts are sensor-out contacts each in electrical communication with a second side of a respective one of the conductive polymeric sensors; and an analytic unit, wherein the analytic unit comprises: an interrogation probe configured to be removably coupled to the interrogation interface by moving the interrogation probe into electrical engagement with the plurality of contacts to obtain a sensor output from each of the conductive polymeric sensors, wherein the sensor output from each of the conductive polymeric sensors is representative of electrical impedance of that particular conductive polymeric sensor; an analog-to-digital converter coupled to the interrogation probe and operative to convert the sensor output from each of the conductive polymeric sensors to digital data; a memory; and a processor coupled to the memory, wherein the memory contains a program that, when executed by the processor, performs a method comprising:

receiving the digital data from the analog-to-digital converter; and analyzing the digital data along with reference data using a multivariate statistical technique to determine a quality classification of the liquid contained in the bottle, wherein the reference data is associated with one or more liquids each of known quality classification.

12. The electronic nose system as recited in claim 11, wherein the mechanical chamber includes a septum that separates the mechanical chamber from the headspace in the inactive state, and wherein the mechanical chamber includes a protruding element configured to be capable of piercing the septum to drive the mechanical chamber from the inactive state to the active state.

13. The electronic nose system as recited in claim 11, wherein the interrogation probe includes a power contact that is configured to engage the power-in contact exposed on the outside surface of the quality-sensing bottle cap, and wherein the interrogation probe further includes a plurality of sensor-in contacts configured to engage the plurality sensor-out contacts exposed on the outside surface of the quality-sensing bottle cap.

14. The electronic nose system as recited in claim 11, wherein analyzing the digital data along with reference data using a multivariate statistical technique to determine a quality classification of the liquid contained in the bottle includes using principal component analysis (PCA) to calculate a first principle component and a second principle component of the digital data and the reference data.

15. The electronic nose system as recited in claim 11, wherein the liquid contained in the bottle is purported to be olive oil, and wherein the one or more liquids each of known quality classification is/are selected from the group consisting of refined olive oils, extra virgin olive oils, lampante olive oils, and combinations thereof.

16. The electronic nose system as recited in claim 11, wherein the liquid contained in the bottle is purported to be olive oil, and wherein the one or more liquids each of known quality classification is/are selected from the group consisting of "fusty" olive oils, "muddy sediment" olive oils, "musty" olive oils, "rancid" olive oils, and combinations thereof.

* * * * *